(12) United States Patent
Geddes et al.

(10) Patent No.: US 7,732,215 B2
(45) Date of Patent: Jun. 8, 2010

(54) CYANIDE SENSING COMPOUNDS AND USES THEREOF

(75) Inventors: Chris D. Geddes, Bel-Air, MD (US); Ramachandram Badugu, Baltimore, MD (US); Joseph R. Lakowicz, Ellicott City, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 692 days.

(21) Appl. No.: 10/572,344

(22) PCT Filed: Sep. 16, 2004

(86) PCT No.: PCT/US2004/030066

§ 371 (c)(1),
(2), (4) Date: May 16, 2007

(87) PCT Pub. No.: WO2005/029033

PCT Pub. Date: Mar. 31, 2005

(65) Prior Publication Data

US 2008/0096281 A1  Apr. 24, 2008

Related U.S. Application Data

(60) Provisional application No. 60/503,689, filed on Sep. 17, 2003.

(51) Int. Cl.
*G01N 33/00* (2006.01)
*C09K 11/06* (2006.01)
*C07F 5/02* (2006.01)

(52) U.S. Cl. ............ 436/109; 252/301.16; 252/301.22; 436/166; 436/172; 564/8; 568/1

(58) Field of Classification Search ............ 252/301.16, 252/301.22; 436/106, 164, 166, 172; 564/8; 568/1
See application file for complete search history.

(56) References Cited

U.S. PATENT DOCUMENTS

| | | | | |
|---|---|---|---|---|
| 3,432,269 A * | 3/1969 | Kramer et al. | ............... | 436/109 |
| 5,116,759 A * | 5/1992 | Klainer et al. | ............ | 435/287.2 |
| 5,503,770 A * | 4/1996 | James et al. | ............ | 252/301.16 |
| 6,462,179 B1 * | 10/2002 | Stolowitz et al. | ......... | 530/391.1 |
| 6,682,938 B1 * | 1/2004 | Satcher et al. | ............... | 436/172 |
| 6,916,660 B2 * | 7/2005 | Wang et al. | ................... | 436/63 |

(Continued)

FOREIGN PATENT DOCUMENTS

WO   WO 2004/024191   3/2004

OTHER PUBLICATIONS

S. I. Baskin and T. G. Brewer, In Medical Aspects of Chemical and Biological Warfare, Eds. F. Sidell, E. T Takafuji and D. R. Franz, TMM publications, Washington, 1997, Chapter 10, p. 271-286.

(Continued)

*Primary Examiner*—Arlen Soderquist
(74) *Attorney, Agent, or Firm*—Marianne Fuierer; Moore & Van Allen, PLLC

(57) ABSTRACT

The present invention relates to a cyanide detection method using fluorescence and cyanide sensitive boronic acid containing fluorophores, wherein a change in a measured fluorescent property correlates to the concentration of the cyanide compound in a biological or environmental test sample.

30 Claims, 28 Drawing Sheets

U.S. PATENT DOCUMENTS

| | | | |
|---|---|---|---|
| 7,095,502 | B2 | 8/2006 | Lakowicz et al. |
| 2002/0031447 | A1* | 3/2002 | Brinz et al. ............... 422/88 |
| 2003/0228682 | A1 | 12/2003 | Lakowicz et al. |
| 2004/0038419 | A1* | 2/2004 | Weiner et al. ............. 436/109 |
| 2004/0087842 | A1* | 5/2004 | Lakowicz et al. .......... 600/317 |
| 2004/0121478 | A1* | 6/2004 | Brinz et al. .............. 436/109 |
| 2007/0274922 | A1* | 11/2007 | Wang et al. ............... 424/9.6 |

OTHER PUBLICATIONS

F. J. Baud, P. Barriot, and V. Toffis (1991). Elevated blood cyanide concentrations in victims of smoke-inhalation. *N. Engl. J. Med.*, 325(25) 1761-1766.

Z. Gryczynski, I. Gryczynski and J. R. Lakowicz, Fluorescence Sensing Methods, *Methods in Enzymology*, 360 (2002) 44-75.

G. J. Kavarnos, Fundamentals of Photoinduced Electron Transfer, VCH, New York, 1993, chapter 4, pp. 185-234.

J. S. Lang, D. Mullin, C. Fenyvesi, R. Rosenberg and J. Barnes (1986). Is the "protector of lions" losing his touch? (Hafez Assad) *US News & World Report*, Nov. 10, 1986 p. 28.

Medical expert reports use of chemical weapons in Iran-Iraq war, *UN Chronicle 22* (May 1985) 24-26.

A. Ishii, H. Seno, K. Watanabe-Suzuki, O. Suzuki and T Kumazawa (1998). Determination of cyanide in whole blood by capillary gas chromatography with cryogenic oven trapping. *Anal. Chem.*, 70(22) 4873-4876.

F. Moriya and Y. Hashimoto (2001). Potential for error when assessing blood cyanide concentrations in fire victims. *J. Forensic Sci.*, 46(6) 1421-1425.

C. J. Clark, D. Campbell and W. H. Reid (1981). Blood carboxyhemoglobin and cyanide levels in fire survivors. *Lancet*, 1(8234) 1332-1335.

D. Keilin (1929). Cytochrome and Respiratory Enzymes. Proc. R. Soc Lond. *B. Biol. Sci.*, 104 206-251.

C. Giuriati, S. Cavalli, A. Gorni, D. Badocco and P. Pastore (2004). Ion chromatographic determination of sulfide and cyanide in real matrices by using pulsed amperometric detection on a silver electrode. *J. Chromato. A*, 1023(1) 105-112.

M. T. Fernandez-Arguelles, J. M. C. Costa-Fernandez, R Pereiro and A. Sanz-Medel (2003). Room temperature phosphorimetric determination of cyanide based on triplet state energy transfer. *Anal. Chim. Acta.*, 491(1) 27-35.

J. D. Favero and M. Tubino (2003). Semi-quantitative "spot-test" of cyanide. *Anal. Sci.*, 19(8) 1139-1143.

J. V. Ros-Lis, R. Martinez-Manez and J. Soto (2002). A selective chromogenic reagent for cyanide determination. *Chem. Commun.*, 19 2248-2249.

K Cho, Y. S Jang, M. S. Gong, K Kim and S. W. Joo (2002). Determination of cyanide species in silver and gold plating solutions by Raman spectroscopy. *Appl. Spectrosc.*, 56(9) 1147-1151.

G. Drochioiu (2002). Highly selective and sensitive reaction of cyanide with 2,2-dihydroxy-1,3-indanedione. *Anal. Bioanal. Chem.*, 372(5-6) 744-747.

C. Hughes, F. Lehner, L. Dirikolu, D. Harkins, J. Boyles, K McDowell, T. Tobin, J. Crutchfield, M. Sebastian, L. Harrison and S. I. Baskin (2003). A simple and highly sensitive spectrophotometric method for the determination of cyanide in equine blood. *Toxicol. Mech. Methods*, 13(2) 129-138.

A. Ipatov, M. Ivanov, S. Makarychev-Mikhailov, V. Kolodnikov, A. Legin and Y. Vlasov (2002). Determination of cyanide using flow-injection multisensor system. *Talanta*, 58(6) 1071-1076.

M. Hoshino, K Nagashima, M. Kamaya and N. Nakano (2003. Spectrophotometric determination of cyanide ion in waste water using copper(II) and N,N-diethyl-p-phenylenediamine. *Bunseki Kagaku*, 52(6) 481-484, abstract and title only.

G. Drochioiu (2002). Fast and highly selective determination of cyanide with 2,2-dihydroxy-1,3-indanedione. *Talanta*, 56(6) 1163-1165.

A. Tracqui, J. S. Raul, A. Geraut, L. Berthelon and B. Ludes (2002). Determination of blood cyanide by HPLC-MS. *J. Anal. Toxicol.*, 26(3) 144-148.

B. Vallejo-Pecharroman and M.D. L. de Castro (2002). Determination of cyanide by a pervaporation-UV photodissociation-potentiometric detection approach. *Analyst*, 127(2) 267-270.

W. R. Premasiri, R. H. Clarke, S. Londhe and M. E. Womble (2001). Determination of cyanide in waste water by low-resolution surface enhanced Raman spectroscopy on sol-gel substrates. *J. Raman Spectrsc.*, 32(11) 919-922.

D. E. Barnes, P. J. Wright, S. M. Graham and E. A. Jones-Watson (2000). Techniques for the determination of cyanide in a process environment: A review. *Geostandards Newsletter—The Journal of Geostandards and Geoanalysis*, 24(2) 183-195.

D. L. Recalde-Ruiz, E. Andres-Garcia and M. E. Daiz-Garcia (2000). Fluorimetric flow injection and flow-through sensing systems for cyanide control in waste water. *Analyst*, 125(11) 2100-2105.

T. Mansfeldt and H. Biernath (2000). Determination of total cyanide in soils by micro-distillation. *Anal. Chim Acta.*, 406(2) 283-288.

E. Nakamura and M. Yagi (2000). Spectrophotometric determination of cyanide with isonicotinic acid sodium barbiturate. *Bunseki Kagaku*, 49(1) 55-58, title and abstract.

E. Miralles, R. Compano, M. Granados and M. D. Prat (2000). Determination of metal-cyanide complexes by ion-interaction chromatography with fluorimetric detection. *Anal. Chim. Act.*, 403(1-2) 197-204.

C. D. Geddes (2001). Optical halide sensing using fluorescence quenching: theory, simulations and applications—a review. *Meas. Sci. Technol.*, 12(9) R53-R88.

R. Badugu, J. R. Lakowicz and C. D. Geddes, *Anal. Biochem.* R. Badugu, J.R. Lakowicz and C.D. Geddes (2004). The non-invasive continuous monitoring of physiological glucose using a novel monosaccharide-sensing contact lens. *Anal Chem.*, 76(3), 610-618.

N. Dicesare and J. R. Lakowicz (2001). Spectral properties of fluorophores combining the boronic acid group with electron donor or withdrawing groups. Implication in the development of fluorescence probes for saccharides. *J. Phys. Chem. A*, 105(28) 6834-6840.

N. Dicesare and J. R. Lakowicz (2002). Charge transfer fluorescent probes using boronic acids for monosaccharide signaling. *J. Biomedical Optics*, 7(4) 538-545.

N. Dicesare and J. R. Lakowicz (2001). Wavelength-ratiometric probes for saccharides based on donor-acceptor diphenylpolyenes. *J. Photochem. Photobiol. A: Chem.*, 143 39-47.

N. DiCesare, D. P. Adhikari, J. J. Heynekamp, M. D. Heagy and J. R. Lakowicz (2002). Spectroscopic and photophysical characterization of fluorescent chemosensors for monosaccharides based on N-phenylboronic acid derivatives of 1,8-naphthalimide. *J. Fluorescence*, 12(2) 147-154.

R. Badugu, J. R Lakowicz and C. D. Geddes (2005). Cyanide-sensitive fluorescent probes. *Dyes & Pigments*, 64(1) 49-55.

R. Badugu, J. R. Lakowicz and C. D. Geddes (2003). A glucose sensing contact lens: a non-invasive technique for continuous physiological glucose monitoring. *J. Fluorescence*, 13(5) 371-374.

N. Dicesare and J.R. Lakowicz (2002). Chalcone-analogue fluorescent probes for saccharides signaling using the boronic acid group. *Tetrahedron Lett.*, 43(14) 2615-2618.

N. Dicesare and J.R. Lakowicz (2001). A new highly fluorescent probe for monosaccharides based on a donor-acceptor diphenyloxazole. *Chem Commun.*, 19 2022-2023.

N. Dicesare and J.R. Lakowicz (2001). New color chemosensors for monosaccharides based on Azo dyes. *Org. Lett.*, 3(24) 3891-3893.

Z. Filipovic-Kovaceic, M. Miksaj and D. Salamon (2002). Cyanide determination in fruit brandies by an amperometric biosensor with immobilised *Saccharomyces cerevisiae*. *Eur. Food Res. Technol.*, 215(4), 347-352.

N. Dicesare and J.R. Lakowicz (2001). Evaluation of two synthetic glucose probes for fluorescence-lifetime-based sensing. *Anal. Biochem.*, 294 154-160.

\* cited by examiner

| Probe | $R^1$ | $R^2$ | $R^3$ | $R^4$ |
|---|---|---|---|---|
| o-BMOQBA | OCH$_3$ | B(OH)$_2$ | H | H |
| m-BMOQBA | OCH$_3$ | H | B(OH)$_2$ | H |
| p-BMOQBA | OCH$_3$ | H | H | B(OH)$_2$ |
| BMOQ | OCH$_3$ | H | H | H |
| o-BMQBA | CH$_3$ | B(OH)$_2$ | H | H |
| m-BMQBA | CH$_3$ | H | B(OH)$_2$ | H |
| p-BMQBA | CH$_3$ | H | H | B(OH)$_2$ |
| BMQ | CH$_3$ | H | H | H |

Table 1 - Dissociation constants, $K_D$ ($\mu M^3$), for the probes with cyanide in water.

| Probe | $K_D$ ($\mu M^3$) |
|---|---|
| o-BMOQBA | 52.9 |
| m-BMOQBA | 84.0 |
| p-BMOQBA | 20.8 |
| BMOQ | --- |
| o-BMQBA | 16.7 |
| m-BMQBA | 16.9 |
| p-BMQBA | 15.9 |
| BMQ | --- |

FIGURE 9

Table 2 – Multiexponential Intensity decay of BMOQ and o-BMOQBA

| [Cyanide] µM | $\tau_1$ (ns) | $\alpha_1$ | $\tau_2$ (ns) | $\alpha_2$ | $\bar{\tau}$ (ns) | $<\tau>$ (ns) | $\chi^2$ |
|---|---|---|---|---|---|---|---|
| *o-BMOQBA | | | | | | | |
| 0 | 26.71 | 1.0 | | | 26.71 | 26.71 | 1.33 |
| 5 | 26.33 | 1.0 | | | 26.33 | 26.33 | 1.13 |
| 10 | 26.34 | 1.0 | | | 26.34 | 26.34 | 1.21 |
| 15 | 26.19 | 1.0 | | | 26.19 | 26.19 | 1.30 |
| 25 | 24.78 | 1.0 | | | 24.78 | 24.78 | 1.23 |
| 35 | 0.324 | 0.0160 | 25.54 | 0.9840 | 25.53 | 25.14 | 1.35 |
| 45 | 0.326 | 0.0184 | 25.10 | 0.9816 | 25.09 | 24.64 | 1.46 |
| 50 | 0.455 | 0.0176 | 25.20 | 0.9824 | 25.19 | 24.76 | 1.41 |
| *BMOQ | | | | | | | |
| 0 | 27.30 | 1.0 | | | 27.30 | 27.30 | 1.08 |
| 5 | 27.04 | 1.0 | | | 27.04 | 27.04 | 1.10 |
| 10 | 26.74 | 1.0 | | | 26.74 | 26.74 | 1.12 |
| 15 | 26.53 | 1.0 | | | 26.53 | 26.53 | 1.06 |
| 20 | 26.25 | 1.0 | | | 26.25 | 26.25 | 1.14 |
| 30 | 25.86 | 1.0 | | | 25.86 | 25.86 | 1.17 |
| 40 | 25.37 | 1.0 | | | 25.37 | 25.37 | 1.05 |
| 50 | 25.00 | 1.0 | | | 25.00 | 25.00 | 1.16 |

* $\lambda_{ex}$ = 372 nm, emission was collected with a 416 nm cut-off filter. BMOQ $K_{SV} \approx 2$ nM$^{-1}$

FIGURE 10

Table 3 – Multiexponential Intensity decay of BMQ and o-BMQBA

| [Cyanide] µM | $\tau_1$ (ns) | $\alpha_1$ | $\tau_2$ (ns) | $\alpha_2$ | $\bar{\tau}$ (ns) | $<\tau>$ (ns) | $\chi^2$ |
|---|---|---|---|---|---|---|---|
| *o-BMQBA | | | | | | | |
| 0 | 2.18 | 0.4646 | 4.74 | 0.5354 | 4.01 | 3.55 | 1.00 |
| 5 | 2.14 | 0.4615 | 4.45 | 0.5385 | 3.78 | 3.38 | 1.12 |
| 10 | 2.28 | 0.5704 | 4.75 | 0.4296 | 3.78 | 3.34 | 1.04 |
| 15 | 1.86 | 0.3265 | 3.64 | 0.6735 | 3.29 | 3.06 | 0.97 |
| 20 | 1.88 | 0.3476 | 3.69 | 0.6524 | 3.30 | 3.06 | 1.04 |
| 30 | 1.44 | 0.1762 | 3.27 | 0.8238 | 3.11 | 2.95 | 1.21 |
| 40 | 1.92 | 0.3511 | 3.59 | 0.6489 | 3.21 | 3.00 | 0.90 |
| 50 | 1.87 | 0.3320 | 3.58 | 0.6680 | 3.22 | 3.01 | 1.07 |
| *BMQ | | | | | | | |
| 0 | 2.59 | 1.0 | | | 2.59 | 2.59 | 1.07 |
| 5 | 2.58 | 1.0 | | | 2.58 | 2.58 | 1.09 |
| 10 | 2.59 | 1.0 | | | 2.59 | 2.59 | 1.07 |
| 15 | 2.57 | 1.0 | | | 2.57 | 2.57 | 1.02 |
| 20 | 2.57 | 1.0 | | | 2.57 | 2.57 | 1.12 |
| 30 | 2.55 | 1.0 | | | 2.55 | 2.55 | 1.08 |
| 40 | 2.55 | 1.0 | | | 2.55 | 2.55 | 1.14 |
| 50 | 2.55 | 1.0 | | | 2.55 | 2.55 | 1.17 |

* $\lambda_{ex}$ = 372 nm, emission was collected with a 416 nm cut-off filter. BMQ $K_{sv}$ ≈ 0.4 nM$^{-1}$

FIGURE 11

| Probe | $R^1$ | $R^2$ | $R^3$ |
|---|---|---|---|
| *o*-BAQBA | B(OH)$_2$ | H | H |
| *m*-BAQBA | H | B(OH)$_2$ | H |
| *p*-BAQBA | H | H | B(OH)$_2$ |
| BAQ | H | H | H |

Table 4: Multiexponential intensity decay of BAQ and o-BAQBA

| [Cyanide] μM | $\tau_1$ (ns) | $\alpha_1$ | $\tau_2$ (ns) | $\alpha_2$ | $\tau_3$ (ns) | $\alpha_3$ | $\bar{\tau}$ | $<\tau>$ | $\chi^2$ |
|---|---|---|---|---|---|---|---|---|---|
| BAQ | | | | | | | | | |
| 0 | 2.48 | 1 | - | - | - | - | 2.48 | 2.48 | 1.10 |
| 2 | 2.48 | 1 | - | - | - | - | 2.48 | 2.48 | 1.02 |
| 4 | 2.49 | 1 | - | - | - | - | 2.49 | 2.49 | 1.19 |
| 6 | 2.49 | 1 | - | - | - | - | 2.49 | 2.49 | 1.32 |
| 10 | 2.49 | 1 | - | - | - | - | 2.49 | 2.49 | 1.18 |
| 16 | 2.49 | 1 | - | - | - | - | 2.49 | 2.49 | 1.28 |
| 20 | 2.47 | 1 | - | - | - | - | 2.47 | 2.47 | 0.89 |
| o-BAQBA | | | | | | | | | |
| (380 nm)[a] | | | | | | | | | |
| 0 | 2.04 | 0.71 | 3.41 | 0.29 | - | - | 2.59 | 2.44 | 1.06 |
| 2 | 2.02 | 0.68 | 3.367 | 0.32 | - | - | 2.61 | 2.45 | 0.99 |
| 4 | 1.98 | 0.67 | 3.37 | 0.33 | - | - | 2.61 | 2.44 | 0.94 |
| 6 | 1.92 | 0.62 | 3.23 | 0.38 | - | - | 2.59 | 2.42 | 1.06 |
| 8[c] | 1.55 | 0.41 | 2.98 | 0.59 | - | - | 2.60 | 2.39 | 1.53 |
| 10[c] | 0.67 | 0.19 | 2.64 | 0.81 | - | - | 2.53 | 2.27 | 2.15 |
| 12.5 | 0.44 | 0.22 | 2.60 | 0.78 | - | - | 2.50 | 2.12 | 2.37 |
| | 0.21 | 0.17 | 2.07 | 0.63 | 3.99 | 0.20 | 2.76 | 2.14 | 1.08 |
| 15 | 0.38 | 0.28 | 2.61 | 0.72 | - | - | 2.49 | 1.98 | 2.18 |
| | 0.21 | 0.23 | 1.85 | 0.44 | 3.46 | 0.32 | 2.71 | 1.97 | 1.01 |
| 20 | 0.38 | 0.30 | 2.65 | 0.70 | - | - | 2.52 | 1.97 | 2.47 |
| | 0.19 | 0.24 | 1.69 | 0.39 | 3.36 | 0.37 | 2.72 | 1.95 | 1.12 |
| (550 nm)[b] | | | | | | | | | |
| 0 | 1.99 | 0.63 | 3.19 | 0.37 | - | - | 2.57 | 2.43 | 0.99 |
| 2 | 1.93 | 0.59 | 3.15 | 0.41 | - | - | 2.58 | 2.43 | 0.98 |
| 4 | 2.04 | 0.70 | 3.39 | 0.30 | - | - | 2.60 | 2.45 | 1.07 |
| 6 | 1.87 | 0.51 | 2.97 | 0.49 | - | - | 2.53 | 2.41 | 1.10 |
| 8 | 1.86 | 0.55 | 3.14 | 0.45 | - | - | 2.60 | 2.44 | 1.01 |
| 10 | 1.75 | 0.48 | 3.10 | 0.52 | - | - | 2.63 | 2.45 | 1.17 |
| 12.5 | 1.85 | 0.61 | 3.48 | 0.39 | - | - | 2.74 | 2.49 | 1.03 |
| 15 | 1.32 | 0.31 | 2.93 | 0.69 | - | - | 2.66 | 2.43 | 1.25 |
| 20 | 1.19 | 0.30 | 2.97 | 0.70 | - | - | 2.71 | 2.44 | 0.92 |

[a] 380 nm long-pass filter.
[b] 550±10 nm interference filter.
[c] No notable improvement in fit could be obtained using a 3-exponent function. Similar values were also found for the *meta*- and *para*-BAQBA probes.

FIGURE 17

CYANIDE SENSING COMPOUNDS AND USES THEREOF

CROSS-REFERENCE TO RELATED APPLICATIONS

This application is filed under the provisions of 35 U.S.C. §371 and claims the priority of International Patent Application No. PCT/US2004/030066 on Sep. 16, 2004, which in turn claims priority of U.S. Provisional Application No. 60/503,689 filed on Sep. 17, 2003.

STATEMENT AS TO FEDERALLY SPONSORED RESEARCH

This invention was made with Government support under RR-08119 awarded by National Institutes of Health. The Government may have certain rights in the invention.

BACKGROUND OF THE INVENTION

1. Field of the Invention

The field of this invention relates generally to the detection, determination, and quantitation of cyanide compounds, and more specifically, to a cyanide detection method using highly fluorescent and cyanide sensitive boronic acid containing fluorophores, wherein a change in a measured fluorescent property correlates to the concentration of the cyanide compound.

2. Background of the Related Art

Cyanide is one of the most lethal poisons known and the toxicity of its salts has been exploited for many hundreds of years. It was not until 1782 that cyanide was identified, isolated by the Swedish Chemist Scheele, who later died from cyanide poisoning [1]. Blood cyanide levels for healthy persons have been reported as being ≈0.3 µM using a gas chromatography method [4], with lethal cyanide blood levels for fire victims in the cyanide concentration range 23-26 µM [4, 5], some 2 orders of magnitude higher than normal healthy blood levels.

More recently, cyanide was unsuccessfully used as a chemical warfare agent in World War 1, primarily because of the way it was delivered [1]. It is also thought to have been used against the inhabitants of the Kurdish city of Hama, Iraq [2], and in Shahabad, Iran, during the Iran-Iraq war [3]. Based on recent cyanide history, acute cyanide poisoning continues to constitute a threat for military forces in future conventional and unconventional conflicts [1].

Cyanide is also readily used in industry in the making of plastics, in the recovery of gold and silver from ores, and in the electroplating of metals, such as silver, gold, platinum and copper [1]. However, while cyanide is used in both military and industrial applications, cyanide poisoning is not common. However, more surprisingly poisoning occurs from smoke inhalation from residential and industrial fires [1, 4, 5], where the combustion of synthetic products that contain carbon and nitrogen, such as plastics and synthetic fibers, release cyanide. There have been numerous studies of fire victims to assess the lethal levels of cyanide [1, 4, 5, 9]. Fire survivors have been found to have <20 uM cyanide in blood, while victims were found to have levels greater than ≈20-30 uM and in some cases as much as 100 uM cyanide [1, 9].

Cigarette smoke also contains cyanide, the nonsmoker typically averages about 0.06 ug/mL (2.31 uM) of cyanide in blood, where as a smoker typically averages 0.17 ug/mL (6.5 uM) [6].

The mechanism of cyanide poisoning is by absorption. Absorption occurs through the lungs, GI track, and even skin. Cyanide's toxicity lies in its ability to inhibit oxygen utilization by cells, binding the ferric iron in cytochrome oxidase [7, 8], thereby blocking the oxidative process of cells. Hence the tissues with the highest oxygen requirement (brain, heart and lungs) are the most affected by acute poisoning.

The estimated intravenous dose that is lethal to 50% of the exposed population ($LD_{50}$) of HCN for a man is 1.0 mg/kg, and the estimated $LD_{50}$ for liquid on the skin is about 100 mg/kg [1]. Hence any cyanide monitoring analytical technique would need a cyanide dynamic range from only few uM to <30 uM to ensure physiological safeguard.

Numerous chemical and physiochemical methods for the detection and determination of cyanides have been used, such as potentiometric, chromatographic, spectrophotometric, flow injection and electrochemical analysis, but only potentiometric determination has been reported as offering continuous cyanide monitoring [48]. Blood cyanide levels for healthy persons have been reported as being ≈0.3 uM using a gas chromatography method [4], with lethal cyanide blood levels for fire victims in the cyanide concentration range 23-26 uM, approximately 100 times higher than normal blood levels. Thus, there are methods for detecting cyanide levels [10-30], but most of these systems are not cheap, portable or field deployable, and most requiring the benefits of an analytical laboratory [10-30].

Fluorescence techniques for sensing a target a fluorescent property, such as lifetime, intensity and wavelength ratiometric sensing [31-33] offer many advantages in the development of miniaturized, cheap, remote, accurate and precise sensors for both laboratory and environmental sensing [31-33]. It is widely accepted that ratiometric or lifetime-based methods offer intrinsic advantages for both chemical and biomedical fluorescence sensing [31, 32]. Fluorescence intensity measurements are typically unreliable away from the laboratory and can require frequent calibration due to a variety of chemical, optical, or other instrumental-related factors. Unfortunately, while fluorescent probes are known to be useful for many applications such as in fluorescence microscopy, fluorescence sensing, and DNA technology, most sensing fluorophores display only changes in intensity in response to analytes and hence relatively few wavelength ratiometric probes are available today.

Some useful wavelength ratiometric probes are available for pH, $Ca^{2+}$, and $Mg^{2+}$, but most generally display small spectral shifts and negligible lifetime changes and are subsequently inadequate for quantitive sensing measurements. Thus, one constraint with fluorescence based cyanide sensing to date, has been the development of suitable probes that show appropriate changes in their fluorescent properties in the 100 nM-30 uM cyanide concentration range.

Accordingly, it would be advantageous to develop new methods for determination of cyanide containing compounds that are sufficiently sensitive to quantitatively determine cyanide levels in biological and environmental samples, wherein the method is simple, cheap and fast to both detect and determine cyanide levels up to physiological lethal/safeguard levels, <20 µM, without the negative aspects of the prior art.

SUMMARY OF THE INVENTION

The present invention generally relates to highly fluorescent and cyanide sensitive boronic acid containing fluorophores and methods of using such fluorophores to detect and quantify the amount of cyanide in biological or environmental test samples In one aspect, the present invention relates to a method for testing a sample for the presence of a cyanide compound, the method comprising:

a) reacting at least one boronic acid containing fluorophore with the sample,
b) illuminating the sample and boronic acid containing fluorophore to generate a response in a fluorescent property; and
c) observing the sample with means for detecting the fluorescent property, wherein a change in the fluorescent property relative to a control value for an unbounded free boronic acid containing fluorophore indicates the presence of cyanide.

The boronic acid containing fluorophores of the present invention may include any boronic acid containing fluorophore which has a sufficient binding affinity for cyanide to essentially exclude other binding compounds. The boronic acid containing fluorophores may include, but are not limited to, the following structures including:

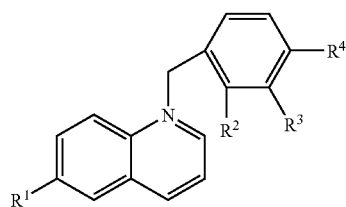

(I)

wherein $R^1$ is H, a straight chain or branched $C_1$-$C_4$ alkyl group, $C_1$-$C_4$ alkoxy group, aryl group, or an amine group $NR^5R^6$, wherein $R^5$ and $R^6$ may be the same as or different from one another and is independently selected from the group consisting of H and $C_1$-$C_4$ alkyl groups, and, $R^2$, $R^3$ and $R^4$ may be the same or different and may be hydrogen or $B(OH)_2$ with the proviso that the compound comprises one $B(OH)_2$ group;

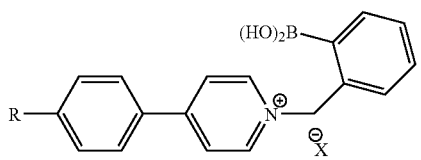

(II)

wherein X is chloride, bromide or iodide, and R is selected from the group consisting of H, straight chain or branched $C_1$-$C_4$ alkyl group, $C_1$-$C_4$ alkoxy group, aryl group, hydroxyl, sulfonyl, and $NR^5R^6$, wherein $R^5$ and $R^6$ may be the same as or different from one another and is independently selected from the group consisting of H and $C_1$-$C_4$ alkyl groups;

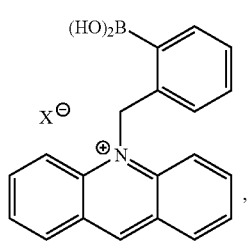

(III)

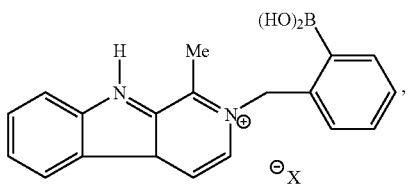

(IV)

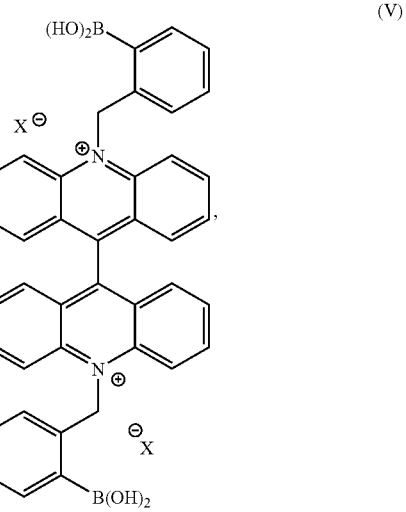

(V)

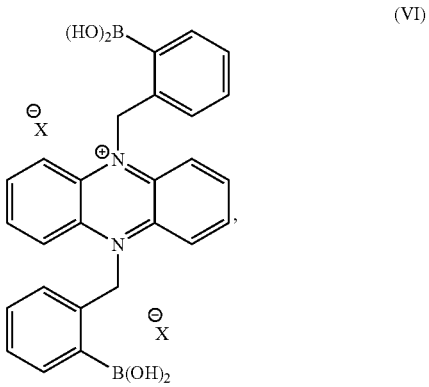

(VI)

wherein X is chloride, bromide or iodide;

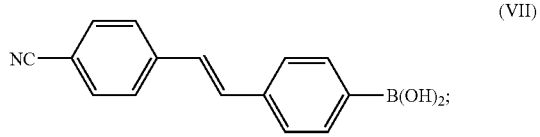

(VII)

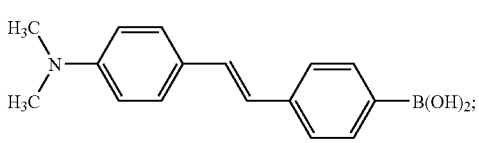

(VIII)

-continued

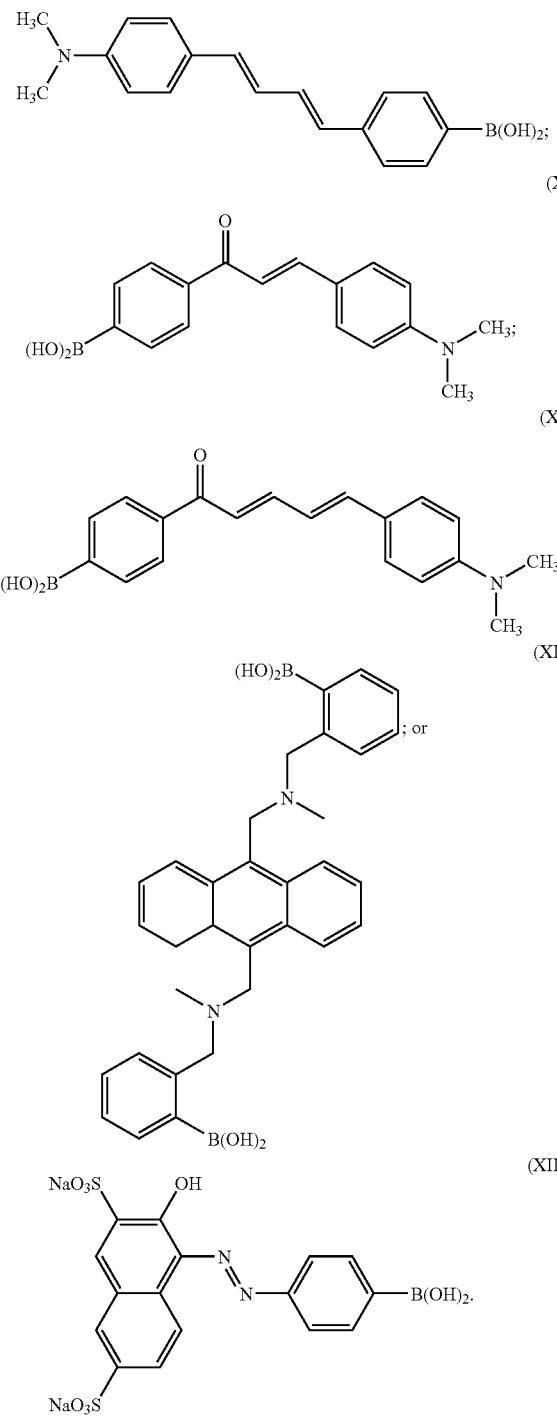

A preferred boronic acid containing fluorophore comprises a fluorescent phenyl boronic acid compound, wherein the fluorophore moiety comprises a heterocyclic quaternary nitrogen (a ring nitrogen) linked through a phenyl ring with the boronic acid moiety.

In another aspect, the present invention relates to a method for testing a biological or environmental test sample for the presence of a cyanide compound, the method comprising:

a) reacting a boronic acid containing fluorophore with the sample,
b) illuminating the sample containing the fluorophore to generate a fluorescent property; and
c) observing the sample with means for detecting the fluorescent property, wherein changes in the fluorescent property indicates the presence of cyanide, wherein the boronic acid containing is present in a concentration of 100 nM to 20 uM; the cyanide is present in a concentration of about 5 uM to about 50 uM; the illuminating step is accomplished using excitation at a range from about 330 to about 370 nm; and the observing step is accomplished using a fluorometer, fluorescence microscope, a laser scanner, or flow cytometer.

In another aspect, the present invention relates to a composition comprising a test sample suspected of containing a cyanide compound and at least one boronic acid containing fluorophore.

In yet another aspect, the present invention relates to kit for detecting and quantifying the amount of cyanide in a test sample, the method comprising:
a container comprising at least one a boronic acid containing fluorophore, wherein the boronic acid containing fluorophore is adhered to a solid support material, impregnated therein or in solution in an amount sufficient to react with any cyanide in a test sample.

In the alternative, the kit may include a solid support material coated with a preferred fluorophore for contact with a test sample suspected of comprising a cyanide compound, wherein the solid support material may include, but not limited to, a non-aqueous matrix which may be a polysaccharide (such as agarose and cellulose); and other mechanically stable matrices such as silica (e.g. controlled pore glass), poly(styrenedivinyl)benzene, polyacrylamide, ceramic particles, optical fibers and derivatives of any of the above. In one embodiment, the solid support material comprises controlled pore glass beads retained in a column that is coated with a preferred fluorophore that has high affinity for a cyanide compound.

The kit may further include an illuminating source and/or a detection instrument, if the fluorescent property change is not triggered by visible light or any changes that are not detectable in the visible range.

Other features and advantages of the invention will be apparent from the following detailed description, drawings and claims.

BRIEF DESCRIPTION OF THE FIGURES

FIG. 9 shows Table 1 that sets forth dissociation constants, $K_D$ (uM$^3$) for the BMQBA, BMOQBA and BMQ probes.

FIG. 10 shows Table 2 that sets forth the values for intensity decay of BMOQ and o-BMOQBA FIG. 11 shows Table 3 that sets forth the values for intensity decay of BMQ and o-BMQBA.

FIG. 17 shows Table 4 that sets forth values for the intensity decay of BAQ and o-BAQBA.

DETAILED DESCRIPTION OF THE INVENTION

Figure 1:
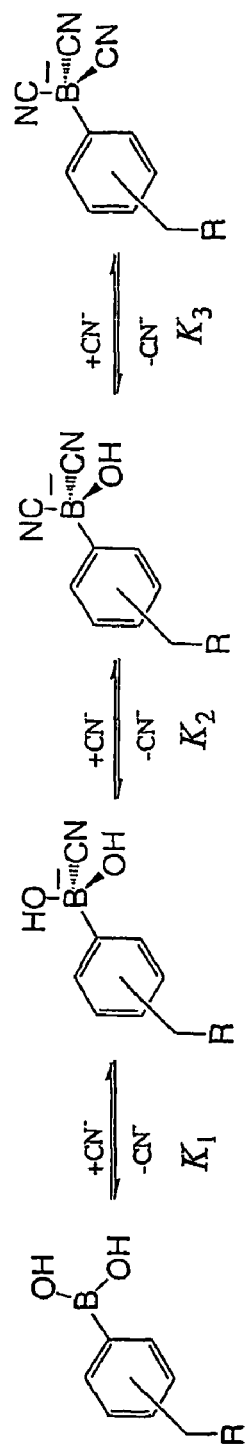
FIG. 1 shows the equilibrium involved in the interaction between a boronic acid group and cyanide.

Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. As employed throughout the disclosure, the following terms shall be understood to have the following meanings.

"Fluorophore," as used herein, is intended to encompass a chemical or biochemical molecule or fragments thereof that is capable of interacting or reacting specifically with a cyanide compound in a test sample to provide one or more optical signals. A preferred embodiment of the invention includes a fluorescent phenyl boronic acid compound, wherein the fluorophore moiety comprises a heterocyclic quaternary nitrogen (a ring nitrogen) linked through a phenyl ring with the boronic acid moiety. Preferred fluorophores are those that are sufficiently water-soluble such that they are useful for assays conducted in aqueous- or partially-aqueous solution. Sufficient solubility is the solubility needed to maintain a useful concentration of both free fluorophores and cyanide-bound forms of the fluorophores in the assay solution, typically a solubility of 0.1 uM to 10 uM.

As used herein, "aryl" is intended to be broadly construed as referring to carbocyclic (e.g., phenyl, naphthyl), as well as heterocyclic aromatic groups (e.g., pyridyl, thienyl, furanyl, etc.), and encompassing unsubstituted as well as substituted aryl groups, wherein the substituents of substituted aryl groups may include any sterically acceptable substituents which are compatible with such aryl groups and which do not preclude the efficacy of the co-solvent compound for its intended utility. Examples of substituents for substituted aryl groups include one or more of halogen (e.g., fluoro, chloro, bromo, and iodo), amino, amido, $C_1$-$C_4$ alkyl, $C_1$-$C_4$ alkoxy, nitro, trifluoromethyl, hydroxy, hydroxyalkyl containing a $C_1$-$C_4$ alkyl moiety, etc.

"Changes in fluorescence," as used herein, encompasses changes in fluorescence lifetime, intensity, emission maxima, absorption maxima, anisotropy, and any measurable parameter associated with fluorescence spectroscopy.

"Ratiometric sensing," as used herein, encompasses comparative fluorescence intensities in the form of a ratio, whereby the numerator and denominator were measured at the same emissive wavelength (if single emission band) or different emissive wavelengths (if dual emission bands or observed red or blue shifts).

The invention described herein generally relates to a method for detecting and quantifying a cyanide compound by changes in fluorescent properties of boronic acid containing fluorophore-sensing moieties. The fluorophore sensing moieties interact or react with a cyanide compound to provide an optical or fluorescent signal, which is indicative of the cyanide concentration in a test sample.

Examples of optical signals include changes in the optical properties, including, but not limited to, a change in color, changes in intensity (absorbance or fluorescence) at the same or different wavelengths, a spectral (absorption or emission) shift, changes in lifetime of luminescence (fluorescence, phosphorescence, and the like).

A preferred fluorophore is a chemical moiety that comprises a boronic acid moiety that, when interacting with a $CN^-$ anion, changes from the neutral form of the boronic acid to the anionic $R$-$B^-$-$(CN)_3$ form, which in turn interacts with an electron deficient (positively charged) quaternary heterocyclic nitrogen center as shown in FIG. 1. Preferably, when the complex is illuminated with visible, ultraviolet or infrared radiation at one wavelength, it will emit radiation at a measurably different wavelength.

A detectable fluorescence response, as used herein, is a change in a fluorescent property of the boronic acid containing fluorophore that is capable of being perceived, either by direct visual observation or instrumentally, and the presence or magnitude of which is a function of the presence of a cyanide compound in the test sample. This change in a fluorescence property may include a change in fluorescence intensity, fluorescence quantum yield, fluorescence polarization, fluorescence lifetime, a shift in excitation or emission wavelength or a combination of these effects. Spectral changes that result in an enhancement or quenching of fluorescence intensity and/or a shift in the wavelength of fluorescence emission or excitation are preferred.

A preferred boronic acid containing fluorophore shows at least a two-fold change in net fluorescence emission intensity (either higher or lower), or a 25% difference in fluorescence lifetime (either shorter or longer).

Alternatively, the binding of cyanide shifts the excitation or emission wavelength of the boronic acid containing fluorophore at least 10 nm (either to shorter or longer wavelength), preferably 25 nm or greater is preferred.

For selected embodiments of the invention, the boronic acid containing fluorophore is highly fluorescent in the absence of the cyanide compound and shows a decrease in fluorescence intensity and fluorescence lifetime upon binding the cyanide compound. In another embodiment of the invention, the boronic acid containing fluorophores have a low fluorescence in a cyanide-free solution and exhibits an increase in fluorescence intensity or fluorescence lifetime upon binding or reacting with a cyanide compound. In yet another embodiment of the invention, the fluorescence intensity remains approximately the same but there is a shift in the excitation or emission spectrum, or both, upon cyanide binding or reacting.

The fluorophore is added to the test sample as in an aqueous or non-aqueous solution or immobilized on a solid or semi-solid support. In either case, the flourophore concentration must be sufficient to generate a detectable fluorescent response in the presence of the cyanide compound. Typically, for a given cyanide compound, the resulting fluorophore solution has a concentration of 100 nm to 20 uM in water or aqueous buffer. More typically, the fluorophore solution has a concentration of 1 uM to 10 uM.

In another embodiment of the invention, the boronic acid containing fluorophore is present by virtue of being immobilized or adsorbed on a solid or semi-solid support. Alternatively, the boronic acid containing fluorophore is present in a gel or other matrix. In this embodiment, contact between the test sample and the boronic acid containing fluorophore optionally requires agitation of the test sample, and/or additional time for the diffusion of cyanide compounds to the boronic acid containing fluorophore.

After addition of the boronic acid containing fluorophore to the test sample, the sample is illuminated by a light source capable of exciting either the free boronic acid containing fluorophore, the boronic acid containing fluorophore-cyanide complex, or both. In those embodiments wherein binding the cyanide compound results in a loss of fluorescence, the observation of a loss of fluorescent signal from the free boronic acid containing fluorophore serves as an indication that the cyanide compound is present. Typically, the sample is excited by a light source capable of producing light at or near the wavelength of maximum absorption of the boronic acid containing fluorophore-cyanide complex. Preferably the sample is excited with a wavelength within 20 nm of the maximum absorption of the boronic acid containing fluorophore-cyanide complex.

Changes in the boronic acid containing fluorophore's fluorescence properties (quantum yield, lifetime, polarization or wavelength) upon binding the cyanide compound are detected qualitatively, or optionally quantitatively, by detection of the resultant light emission. Many techniques are known to those in the art for measuring the time dependence of fluorescence emission, including streak cameras, time correlated single photon counting, direct measurement of the time resolved fluorescence, upconversion techniques, phase-sensitive detection, boxcar techniques, and the like. Similarly, while lasers as light sources and photomultiplier tubes as detectors have been used, for some applications adequate or improved performance may be achieved by the use of LED's, laser diodes, electroluminescent sources, arc lamps, spark gaps, xenon arc lamps, incandescent lamps, or other sources. In the same fashion other light detectors may be used, including microchannel plate photomultiplier tubes, photodiodes, avalanche photodiodes, streak cameras, CCD's and other detectors known to the art may be used.

In another embodiment, the step of observing is optionally made remotely by incorporation of the boronic acid containing fluorophore as part of a fiber optic probe. In this embodiment of the invention, the boronic acid containing fluorophore is attached to the fiber optic probe material, typically glass or functionalized glass (e.g., aminopropyl glass) or the boronic acid containing fluorophore is attached to the fiber optic probe via an intermediate polymer, such as polyacrylamide. The observation of a detectable change in the fluorescence properties of the boronic acid containing fluorophore (detectable fluorescence response) is optionally used to simply identify the presence of the cyanide in the test sample.

Alternatively, the detectable fluorescence response is quantified and used to measure the concentration of the cyanide in the test sample. Quantification may be performed by comparison of the fluorescence response to a standard, or calibration, curve. The standard curve is generated according to methods known in the art using varying and known amounts of the cyanide in standard solutions.

The measurement of quenching can be determined by techniques well known to those in the art, including measuring the change in fluorescence lifetime, fluorescence intensity, excitation spectrum of the donor, or fluorescence dichroism. The preferred embodiment of this invention is to measure the change in fluorescence lifetime which provides a more precise and artifact-free measurement than other methods. It is also preferable to measure these time-dependent changes by phase fluorometry, which is also called phase-modulation fluorometry, or frequency-domain fluorometry. The proportion of short lifetime emitters attributed to the bound form of the macromolecule can be correlated with a unique phase angle and demodulation ratio at some suitable modulation frequency. The proportions of each form (bound vs. unbound) can be determined by measuring phase shifts and demodulations over a suitably wide range of frequencies and fitting them to decay law (Lakowicz, J. R. and I. Gryczynski, "Frequency-Domain Fluorescence Spectroscopy," in Topics in Fluorescence Spectroscopy Vol I: Techniques (J. R Lakowicz, ed.) New York, Plenum Press, pp. 293-336).

The invention is further illustrated in the following examples, which are not intended to be in any way limiting to the scope of the invention as claimed.

EXAMPLE 1

Fluorescence spectra were collected on a Varian eclipse spectrofluorometer with solution optical densities less than 0.2 and $\lambda_{ex}$=345 and 320 nm for BMOQBA and BMQBA, respectively.

Stability (Ks-units uM$^{-3}$ or mol$^{-3}$ dm$^9$ for CN$^-$ and mM$^{-1}$ or mol$^{-1}$ dm$^3$ for glucose and fructose) and Dissociation constants (KD) were obtained by fitting the titration curves with aqueous sodium cyanide to the relation:

$$I = \frac{I_{min} + I_{max} K_s [\text{cyanide}]}{1 + K_s [\text{cyanide}]} \quad (1)$$

where $I_{min}$ and $I_{max}$ are the initial (no cyanide) and final (plateau) fluorescence intensities of the titration curves, where $K_D = (1/K_S)$.

Time-resolved intensity decays were measured using reverse start-stop time-correlated single-photon counting (TCSPC) [31] with a Becker and Hicki gmbh 630 SPC PC card and an un-amplifed MCP-PMT. Vertically polarized excitation at 372 run was obtained using a pulsed LED source (1 MHz repetition rate) and a sheet polarizer. The instrumental response function was ≈1.1 ns fwhm. The emission was collected at the magic angle (54.7°) using a long pass filter (Edmund Scientific), which cut off wavelengths below 416 mn.

The intensity decays were analyzed in terms of the multi-exponential model [31]:

$$I(t) = \Sigma_i \alpha_i \exp(-t/\tau_i), \quad (2)$$

where $\alpha_i$ are the amplitudes and $\tau_i$ the decay times, $\Sigma \alpha_{i=1.0}$.

The fractional contribution of each component to the steady-state intensity is given by:

$$f_i = \frac{\alpha_i \tau_i}{\sum_i \alpha_i \tau_i}. \quad (3)$$

The mean lifetime of the excited state is given by:

$$\bar{\tau} = \sum_i f_i \tau_i \quad (4)$$

and the amplitude-weighted lifetime is given by:

$$<\Sigma> = \Sigma_i \alpha_i \tau_i. \quad (5)$$

The values of $\alpha_i$ and $\tau_i$ were determined by non-linear least squares impulse reconvolution with a goodness-of-fit $\chi^2 R$ criterion. [31]

Steady-state and time-resolved (lifetime) based Stern-Volmer constants were obtained using the well-known Stern-Volmer relationship [33]:

$$I'/I = \tau_O/\tau = 1 + K_{SV}[\text{Cyanide}] \quad (6)$$

where I' and $\tau_O$ are the intensities and lifetimes in the absence of cyanide respectively, and $K_{SV}$ is the Stern-Volmer constant, M$^{-1}$. For detailed descriptions and applications of the Stern-Volmer relation, see [31, 33] and references therein.

Preparation of o-, m- and p-N-(boronobenzyl)6-methylquinolinium bromide (BMQBA) and N-benzyl-6-methylquinolinium bromide (BMQ)

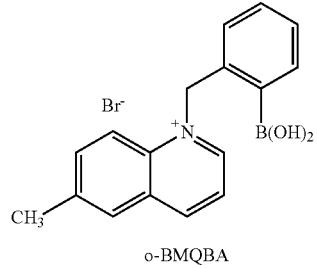

o-BMQBA

The boronic acid containing fluorescent molecular sensing moieties o-, m- and p-BMQBA and the control compound BMQ were prepared using the following generic one step synthetic procedure, described herein for BMQ. Equimolar amounts of 6-methylquinoline and benzylbromide were dissolved in 10 mL dry acetonitrile in a 25 mL round bottomed flask equipped with a magnetic stirrer. The reaction mixture was allowed to stir under an inert atmosphere for 24 hrs at room temperature. During this time, a quantitative amount of quaternized salt was precipitated as a colorless solid. The solid product recovered by filtration was washed several times with dry acetonitrile and then dried under vacuum for 12 hrs. BMQ $^1$H NMR (D$_2$O) δ (ppm): 2.5 (s, 3H); 6.2 (s, 2H); 7.2-7.5 (m, 5H), 7.8 (d, 1H); 8.0 (m, 2H); 8.15 (d, 1H); 9.0 (d, 1H); and 9.3 (d, 1H). HRMS (FAB+, H$_2$O) m/e calculated: 234.1283 (M$^+$-Br), found: 234.1291 (M$^+$-Br).

The corresponding o-, m- and p-boronobenzyl bromides are employed instead of benzyl bromide to obtain the isomeric boronic acid derivatives o-, m- and p-BMQBA, respectively. o-BMQBA $^1$H NMR (D$_2$O) δ (ppm): 2.7 (s, 3H); 6.5 (s, 2H); 7.1 (s, 1H), 7.4-7.5 (m, 2H); 8.0-8.3 (m, 4H); 8.5 (d, 1H); 8.95 (d, 1H); and 9.2 (d, 1H). HRMS (FAB+, H$_2$O) m/e calculated: 346.1978 (M+-Br), found: 346.1960 (M+-Br). m-BMQBA $^1$H NMR (D$_2$O) δ (ppm): 2.5 (s, 3H); 6.2 (s, 2H); 7.3-7.5 (m, 2H), 7.6 (s, 1H); 7.7 (d, 1H); 7.9 (d, 1H); 8.0 (m, 2H); 8.2 (d, 1H); 9.0 (d, 1H) and 9.25 (d, 1H). HRMS (FAB+, H$_2$O) m/e calculated: 346.1978 (M+-Br), found: 346.1988 (M+-Br). p-BMQBA $^1$H NMR (D$_2$O) δ (ppm): 2.55 (s, 3H); 6.2 (s, 2H); 7.25 (d, 2H), 7.7 (d, 2H); 7.9 (t, 1H); 8.0-8.2 (m, 3H); 9.0 (d, 1H); and 9.25 (d, 1H). HRMS (FAB+, H$_2$O) m/e calculated: 346.1978 (M+-Br), found: 346.1960 (M+-Br).

Preparation of o-, m- and p-N-(boronobenzyl)-6-methoxyquinolinium bromide (BMOQBA) and N-benzyl-6-methoxyquinolinium bromide (BMOQ)

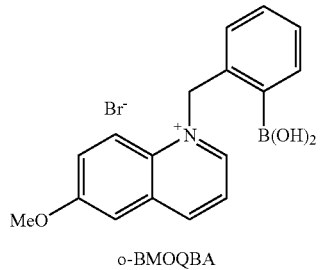

o-BMOQBA

The control compound BMOQ was conveniently prepared using the generic one-step procedure described above for the synthesis of BMQ, wherein 6-methoxyquinoline was used instead of 6-methylquinoline. BMOQ $^1$H NMR (CD$_3$OD) δ (ppm): 4.1 (s, 3H); 6.3 (s, 2H); 7.3-7.5 (m, 5H); 7.85 (m, 2H); 8.15 (t, 1H); 8.45 (d, 1H); 9.2 (d, 1H) and 9.4 (d, 1H). HRMS (FAB+, H$_2$O) m/e calculated: 250.1232 (M+-Br), found: 250.1222 (M+-Br).

The corresponding o-, m- and p-boronobenzyl bromides are employed instead of benzyl bromide to obtain the isomeric boronic acid derivatives o-, m- and p-BMOQBA, respectively. o-BMOQBA $^1$H NMR (CD$_3$OD) δ (ppm): 4.05 (s, 3H); 6.5 (s, 2H); 7.1 (s, 1H); 7.3-7.5 (m, 2H); 7.8-8.0 (m, 4H); 8.5 (t, 1H); 8.8 (d, 1H) and 9.1 (d, 1H). HRMS (FAB+, H$_2$O) m/e calculated: 362.1927 (M+-Br), found: 362.1960 (M+-Br). m-BMOQBA $^1$H NMR (CD$_3$OD) δ (ppm): 4.0 (s, 3H); 6.2 (s, 2H); 7.35-7.55 (m, 2H); 7.6-7.8 (m, 4H); 8.0 (t, 1H); 8.25 (d, 1H); 8.95 (d, 1H) and 9.15 (d, 1H). HRMS (FAB+, H$_2$O) m/e calculated: 362.1927 (M+-Br), found: 362.1848 (M+-Br). p-BMOQBA $^1$H NMR (CD$_3$OD) δ (ppm): 4.0 (s, 3H); 6.2 (s, 2H); 7.25 (d, 2H), 7.5-7.8 (m, 4H); 8.0 (t, 1H); 8.2 (d, 1H); 8.95 (d, 1H) and 9.15 (d, 1H). HRMS (FAB+, H$_2$O) m/e calculated: 362.1927 (M+-Br), found: 362.1956 (M+-Br).

Figure 2:
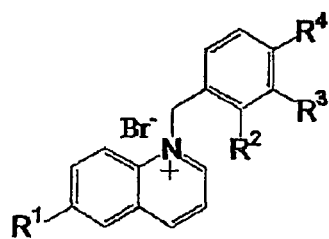
FIG. 2 shows the molecular structure of the ortho, meta and para-BMOQBA and BMQBA probes and the respective control compounds BMOQ and BMQ, which do contain the boronic acid functional group.

FIGS. 3A and B show the absorption and emission spectra of o-BMOQBA (A) and o-BMQBA (B) in water, where the spectra are representative of the other respective isomers shown in FIG. 2. The o-BMOQBA shows a ≈100 nm Stokes-shifted fluorescence band at 450 nm, while the BMQBAs show ≈120 nm. The differences in the absorption spectra can be attributed to the n→π* absorption band of the methoxy oxygen in the 6-position on the quinoline backbone. The large Stokes shifts for these probes is ideal for fluorescence sensing, providing for both an easy discrimination between excitation and observation wavelengths, and the possible use of LED's as cheap excitation sources, which are well-known to be both spectrally and temporally broad [31]. A 372 nm pulsed LED was used for the time-resolved studies, described later.

FIGS. 4A, B and C show the emission spectra of the 3 BMOQBA isomers for increasing cyanide concentrations, with $\lambda_{ex}$=345 nm. As the cyanide concentration increases, the emission band at 450 nm decreases. For the control compound, BMOQ, only a very slight decrease in emission intensity was typically observed for increasing cyanide concentrations, which was attributed to dynamic fluorescence quenching (see lifetime data) by cyanide. FIG. 5A, shows that BMOQ does not possess a boronic acid group and therefore can not bind cyanide as postulated in our recent reports [34, 41]. By plotting the intensity of BMOQ in the presence of cyanide, normalized by the intensity in the absence of cyanide, the Stern-Volmer quenching constant was subsequently determined to be ≈3 nM$^{-1}$, c.f. equation 6.

Figure 4:
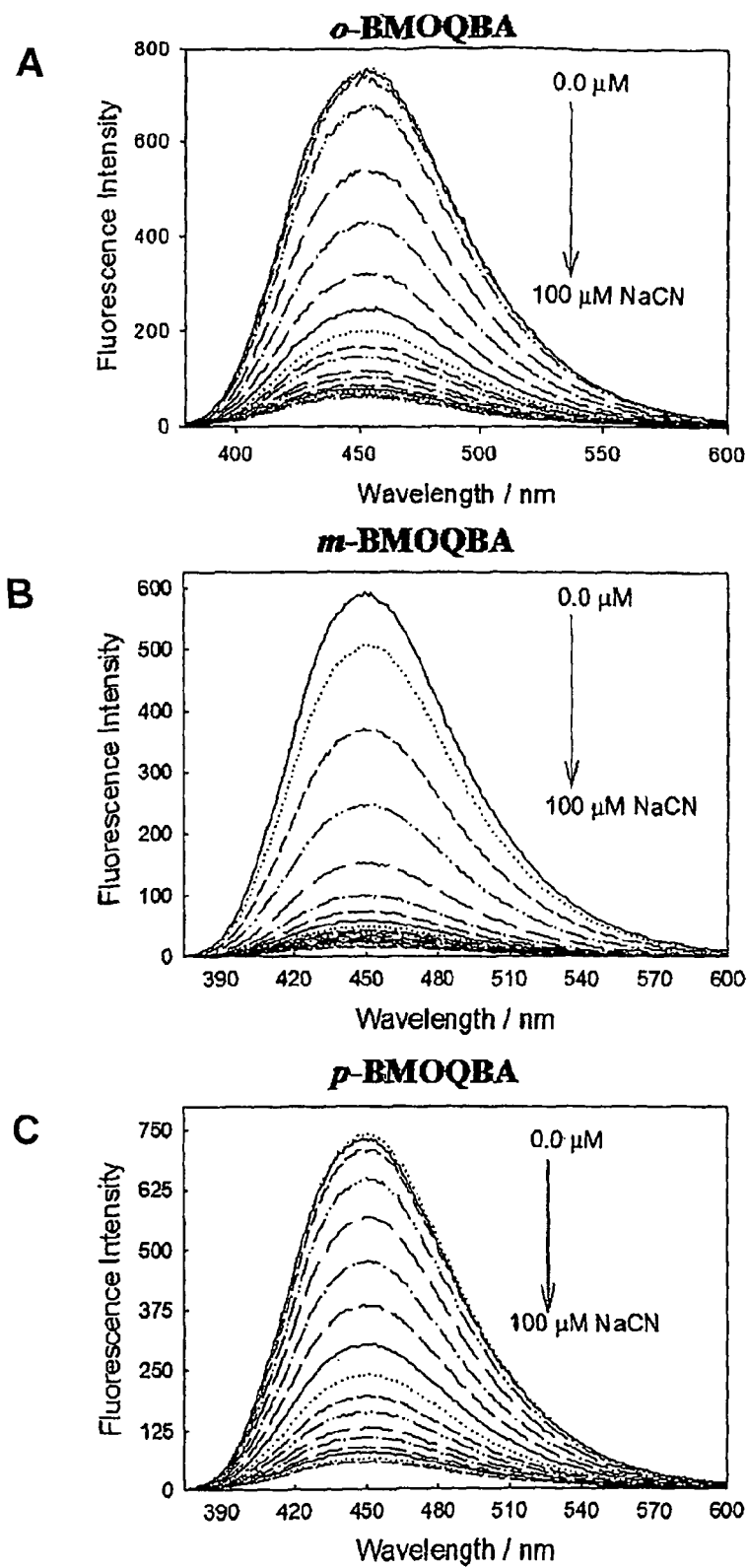
FIGS. 4A, B and C show the emission spectra of o, m, p-BMOQBA in the presence of increasing cyanide concentrations. $\lambda_{ex}=345$ nm.
Figure 5:
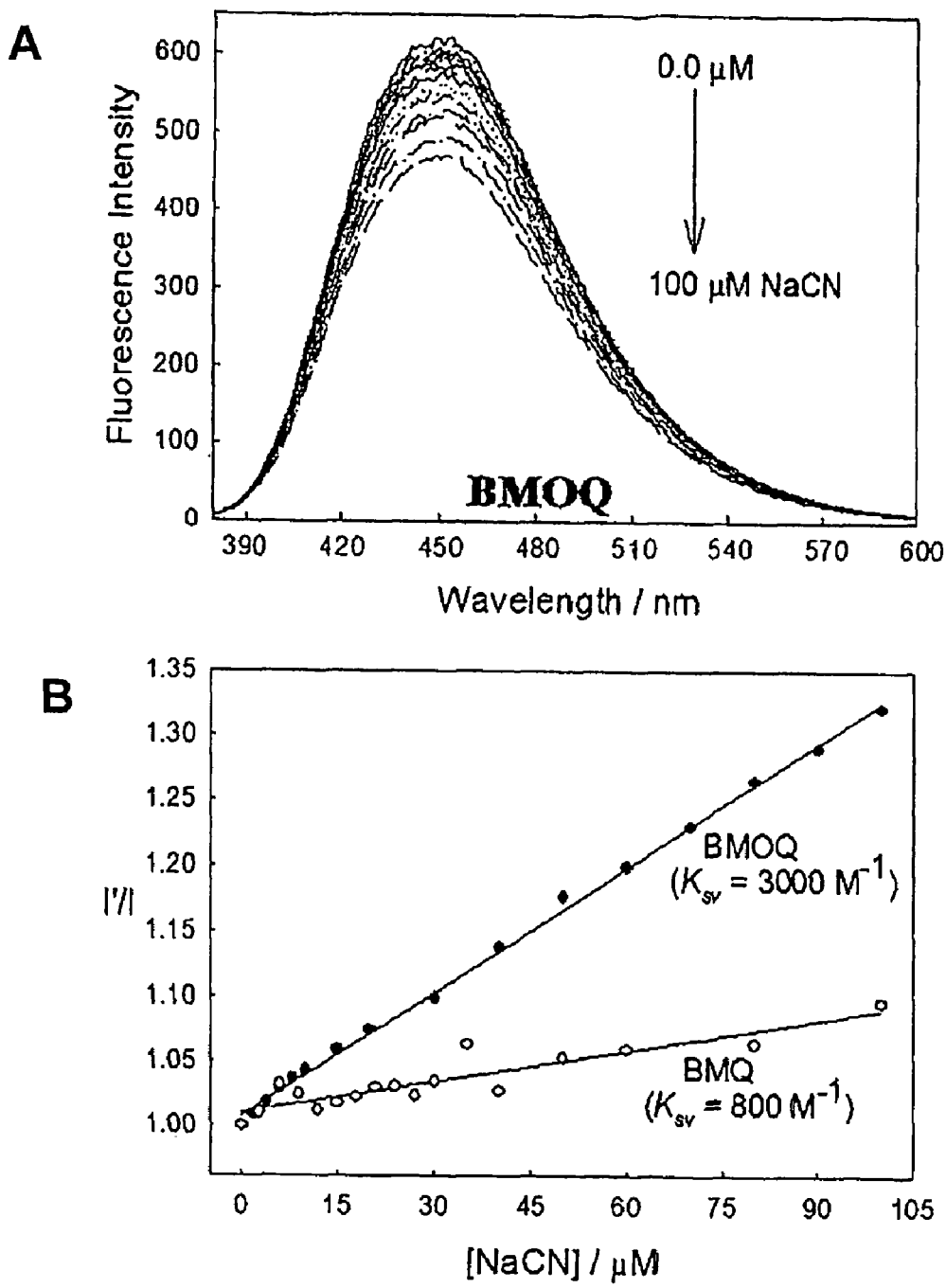
FIGS. 5A and B show the emission spectrum of the control compound BMOQ with increasing cyanide concentrations, (A) ($\lambda_{ex}=345$ nm) and the respective Stern-Volmer like plots for both BMOQ and BMQ, where I' and I are the fluorescence intensities at 450 nm in the absence and presence of cyanide respectively, (B).
Figure 6:
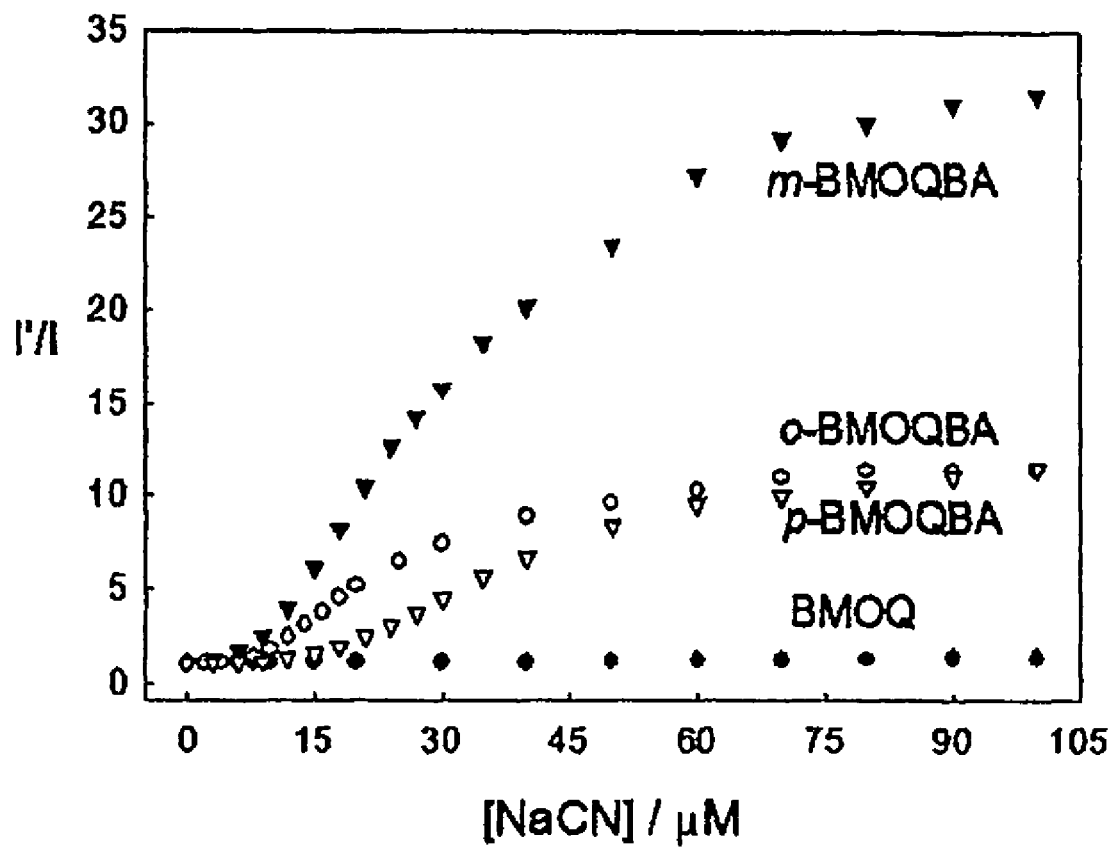
FIG. 6 shows the response of the BMOQBA probes and BMOQ towards aqueous cyanide, where I' and I are the fluorescence intensities at 450 nm in the absence and presence of cyanide respectively.

From the data shown in FIG. 4, intensity ratiometric type plots were constructed, i.e. the intensity in the absence of cyanide divided by the intensity in the presence of cyanide, as set forth in FIG. 6. Interestingly the m-BMOQBA isomer shows a much stronger response to cyanide with a 10-fold intensity change with as little as 20 uM cyanide. Using equation 1 and the data in FIG. 6, the cyanide dissociation constants were determined for the ortho, meta and para boronic acid probes to be 52.9, 84.0 and 20.8 uM$^3$, as set forth in Table 1 and shown in FIG. 9, noting the units uM$^3$ or mol$^3$ dm$^{-9}$ based on the equilibrium shown in FIG. 1. These responses are most encouraging and suggest the use of these isomers for physiological cyanide safeguard. In addition, m-BMOQBA may find applications for cyanide determination post-mortem for fire victims, where cyanide levels exceed the 20 uM lethal concentration threshold [1, 4, 5, 9].

To understand the different responses of the isomers towards cyanide it is informative to consider the charge neutralization-stabilization mechanism of these probes, which was recently reported for glucose [39, 40, 42]. Upon binding, the electron density on the boron atom of the probe is increased, as shown in FIG. 1, facilitating the partial neutralization of the positively charged quaternary nitrogen of the quinolinium moiety. The quaternary nitrogen not only reduces the pKa of the probe [39, 40], but also stabilizes the boronate-cyanide complex formed upon cyanide addition. The differences in cyanide sensitivity between the isomers is explained by either their through-space or through-bound interactions [43, 44] with the positively charged nitrogen, the meta form of the probes thought to interact via both mechanisms [43, 44].

Figure 7:
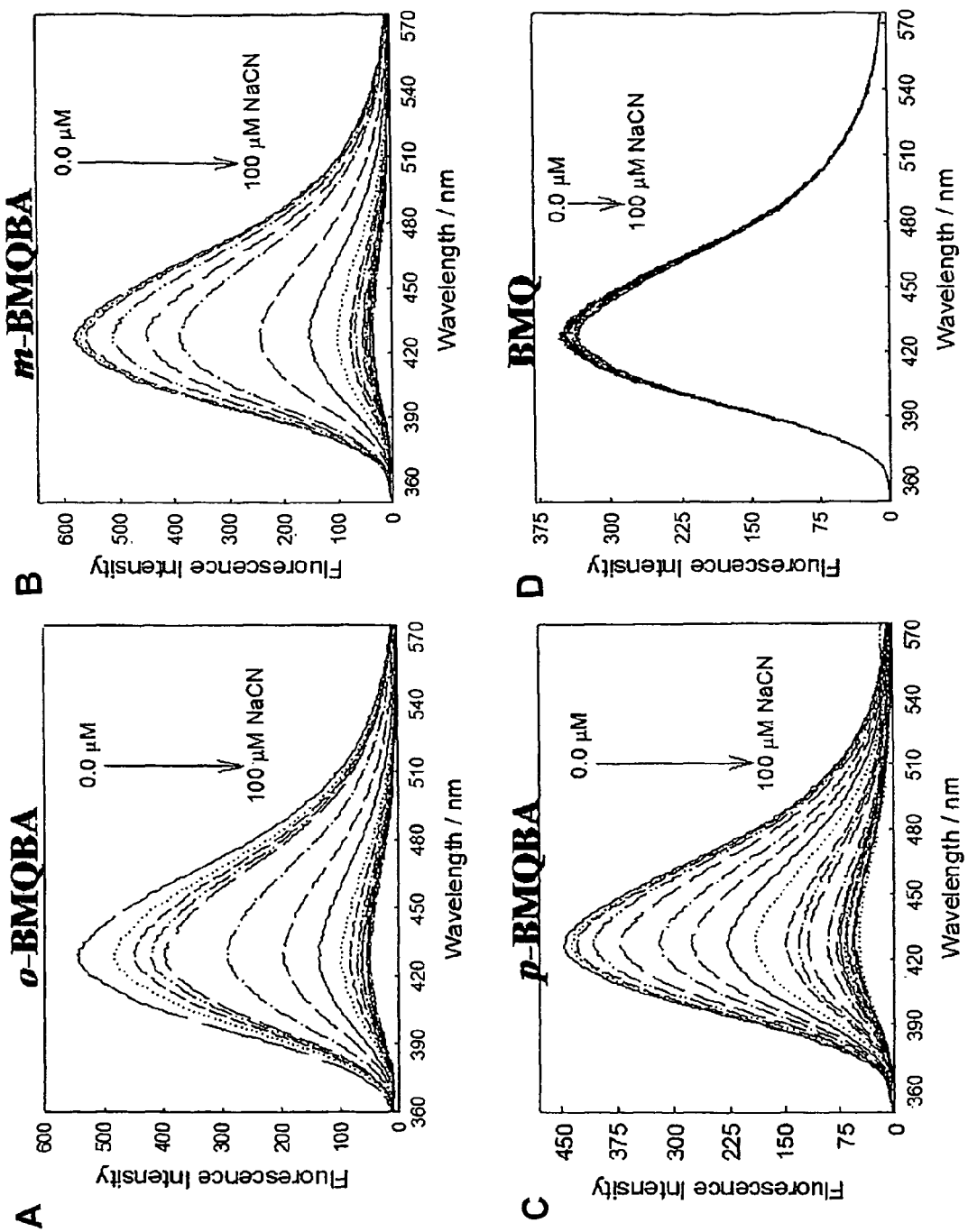
FIGS. 7A, B, C and D show the emission spectra of o, m, p-BMQBA and the control compound BMQ, in the presence of increasing cyanide concentrations. $\lambda_{ex}$=320 nm.
Figure 8:
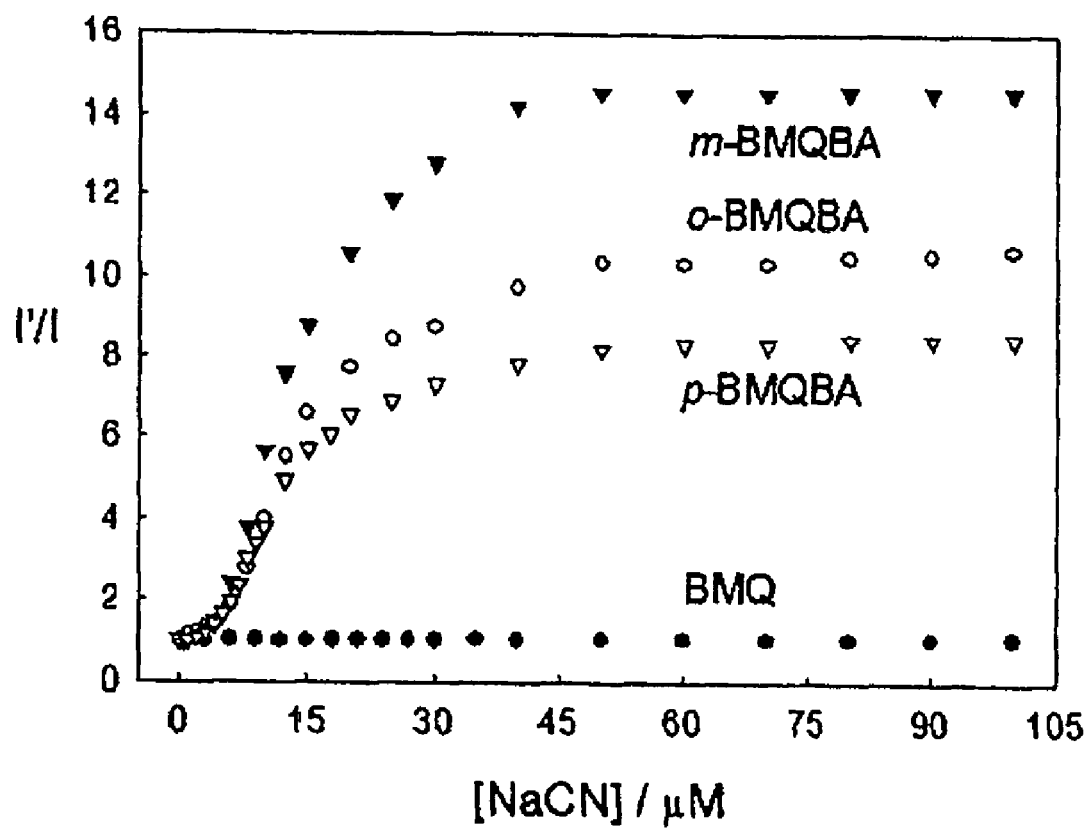
FIG. 8 shows the response of the BMQBA probes and BMQ towards aqueous cyanide, where I' and I are the fluorescence intensities at 450 nm in the absence and presence of cyanide respectively.

FIGS. 7A, B, C and D show the emission spectra for the BMQBA probes and the control compound BMQ for increasing cyanide concentrations. Similarly to the BMOQBA probes, the BMQBA probes show a notable decrease in fluorescence intensity with uM cyanide concentrations. BMQ is however relatively unperturbed, with a Stern-Volmer constant smaller than for BMOQ, FIG. 4, ≈0.8 nM$^{-1}$. Again intensity ratiometric type plots were constructed for the data shown in FIG. 7. FIG. 8 shows a ≈12-fold decrease in fluorescence intensity with 30 uM cyanide for m-BMBQA, ideal for cyanide physiological safeguard monitoring. Interestingly, the response of m-BMOQBA shows twice the response with 75 uM cyanide as compared to the m-BMQBA probe. This notable difference was attributed to the difference in electron donating capabilities between the methyl and methoxy groups in the 6-position on the quinolinium backbone and the resultant charge on the quaternary nitrogen heterocyclic center. This is also reflected in the quantum yields of the probes, with m-BMOQBA having a quantum yield of 0.51 as compared to 0.025 for m-BMQBA. The quantum yield values were determined from a spectral comparison with N-(3 sulfopropyl)-6-methoxyquinolinium, where $\phi_f$=0.53 in water [31, 33].

With notable changes in the fluorescence intensities of the probes in the presence of cyanide it was questioned whether changes in the mean lifetime of the probe would also provide for lifetime based sensing. The reasoning was based on a recent report of a similar probe, based on the 6-amino quinoline nucleus, which showed both spectral shifts and intensity changes in the presence of cyanide, allowing for both excitation and emission wavelength-ratiometric cyanide sensing [34]. The dual emission bands enabled the present inventors previously to clearly resolve the lifetime of both the cyanide bound and unbound probe forms where it was concluded that the bound form had a much shorter lifetime, a few hundred ps, in comparison to the unbound form which had a mean lifetime of 2.59 ns. The measured values of the lifetimes of the BMOQBA and BMQBA probes was determined using the well-known Time-correlated Single Photon Timing Technique, TCSPC [31], and shown in Tables 2 and 3, FIGS. 10 and 11, respectively.

The lifetime of o-BMOQBA was found to be monoexponential in water with a lifetime of 26.71 ns, (Table 2). However in the presence of cyanide the intensity decay is biexponential with a much shorter component now present, ≈300-450 ps. This has the result of reducing the mean lifetime by 4-8% over the range of physiological cyanide importance. Interestingly these measurements were undertaken with a pulsed UV LED with an emission centered at 372 nm, suggesting the utility of the BMOQBA and BMQBA probes for potential use in low power, field-deployable poison safeguard devices. Similar findings were observed for the other isomers.

The lifetime of the control compound BMOQ is monoexponential both in water and in the presence of cyanide, decreasing from 27.30→25.0 ns with up to 50 uM cyanide. In comparison, the lifetime of o-BMOQBA in water was found to be slightly shorter, 26.71 ns. Using equation 6, the dynamic quenching Stern-Vohmer constant was calculated to be ≈2 $nM^{-1}$, very similar to the value obtained from the intensity-based measurements shown in FIG. 5. The decrease in fluorescence intensity shown in FIG. 5A was assigned to dynamic fluorescence quenching by cyanide. Interestingly the presence of a much shorter lifetime component for o-BMOQBA with cyanide, suggests more than a simple collisional quenching process is present. Given this, and the fact that the intensity rapidly decreases in the presence of cyanide, it is speculated that the cyanide bound probe has both a short lifetime, and a significantly reduced quantum yield as compared to the unbound probe form.

Table 3 as set forth in FIG. 11 shows the intensity decay kinetics of BMQ and o-BMQBA. The control compound BMQ was found to be monoexponential in water with a lifetime of 2.59 ns. The presence of cyanide results in a slight decrease in the lifetime, the Stern-Volmer quenching constant 0.4 $nM^{-1}$, not unlike that determined from the intensity plots, FIGS. 5 and 7. The intensity decay of o-BMQBA was found to be biexponential in water, with the mean lifetime decreasing from 4.01 to 3.22 ns in the presence of 50 uM cyanide, a 25% change in mean lifetime which can not be explained by dynamic cyanide quenching, and is therefore attributed to the cyanide bound form. Similar findings were observed for the other isomers. In this analysis it is recognized the complexity of assigning the cyanide bound lifetimes, as three possible bound probe forms are possible as shown in FIG. 1, and as such, all three bound forms are referred to as simply the cyanide bound form.

Clearly the BMOQBA and BMQBA probes characterized herein have the advantage of showing both intensity and lifetime based changes to physiologically important cyanide concentrations, both sets of probes bringing new advantages to fluorescent probes for cyanide determination.

Figure 3:
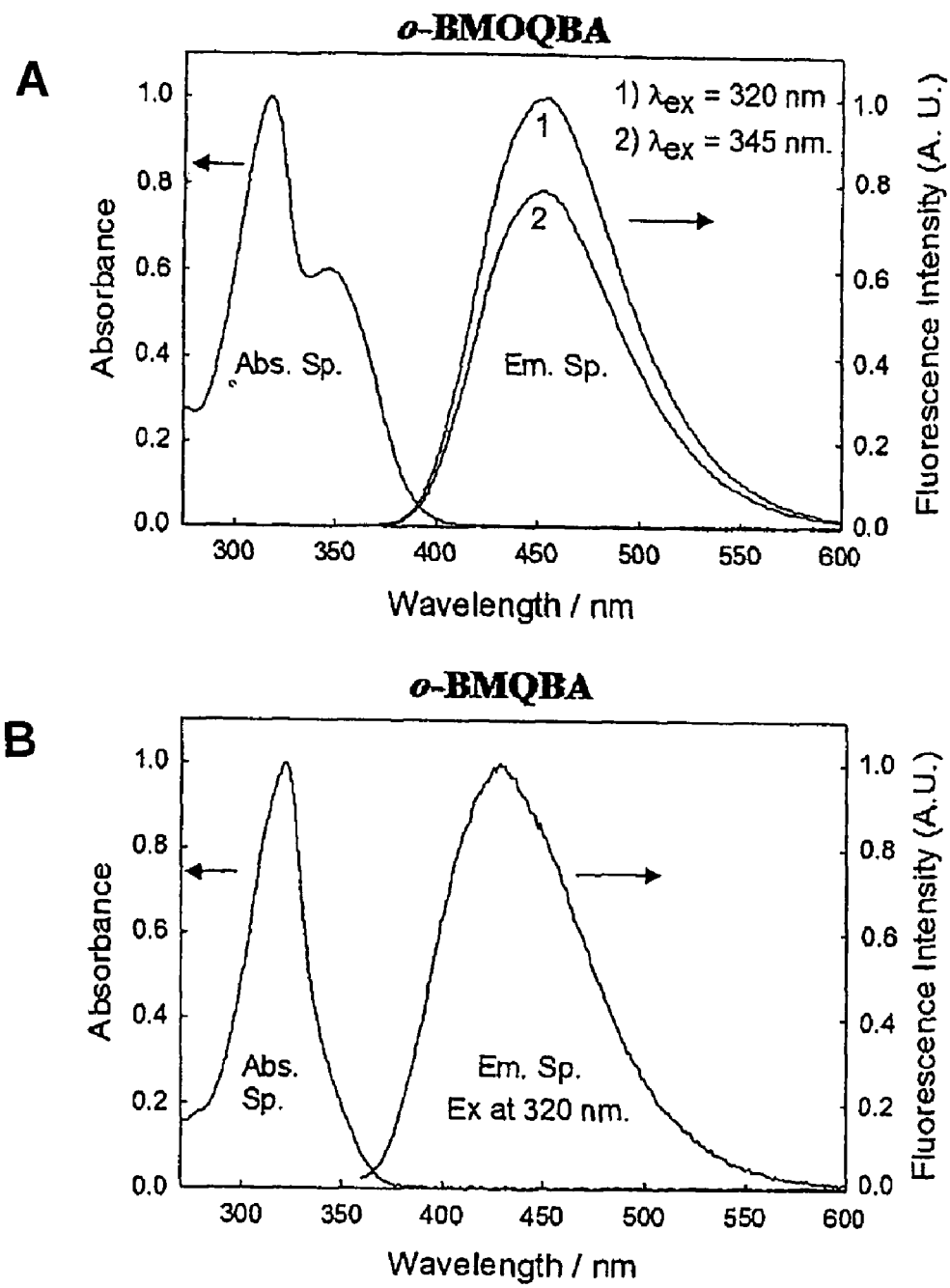
FIGS. 3A and B show the absorption and emission spectra of aqueous o-BMOQBA and o-BMQBA. The spectra are representative of the other respective isomers.

The BMOQBAs typically display a greater dynamic range for sensing, with notable changes observed in the cyanide concentration range from about 5 uM to about 60 uM. The BMOQBAs are highly water-soluble and can be prepared in a one step synthesis. The 350 nm absorption band readily allows for UV LED excitation or even 370/400 nm laser diode excitation, which would not be possible with the BMQBAs (FIG. 3 B). The long lifetime of the BMOQBAs (≈26 ns) accounts for the cyanide collisional quenching, also observed with the control compound BMOQ. Subsequently, these probes are likely to be susceptible to other interferences such as aqueous chloride or oxygen [31, 33]. With regard to interferences by physiological monosaccharides, the dissociation constants have been determined for the ortho, meta and para forms to be 49.5, 1000 and 430 mM for glucose, and 0.66, 1.8 and 9.1 mM for fructose, respectively. Fructose, as expected, shows a greater affinity for the monophenyl boronic acid probes [36], but both sugars are not expected to interfere given the more efficient binding of cyanide.

The BMQBA probes also show notable changes in fluorescence intensity in the presence of 30 uM cyanide, 14 to 8-fold, for the ortho→para isomers respectively. Unlike the BMOQBA probes, this class of probes shows a biexponential lifetime in water, and a relatively much shorter mean lifetime (4.01 ns) that typically decreases 25% with the addition of 50 uM cyanide. The lifetime reduction is thought to be due to the cyanide bound form, given the very minor changes observed with the control compound BMQ. Interestingly, these probes are not likely to be perturbed much by other collisional quenchers due to their short lifetimes. With regard to fluorescence lifetime sensing, these changes are readily detectable using simple and cheap instrumentation [31]. The dissociation constants of the ortho, meta and para forms of BMQBA were found to be 100, 476 and 370 mM for glucose, and 4.7, 13.2 and 13.8 mM respectively for fructose. One particular disadvantage of these probes however, is their requirement for UV excitation at 320 nm, which while possible with LEDs as shown here, to some degree limits their practical use in rapid analysis, portable, field deployable devices, areas of active research [10-30].

EXAMPLE 2

Figure 12:
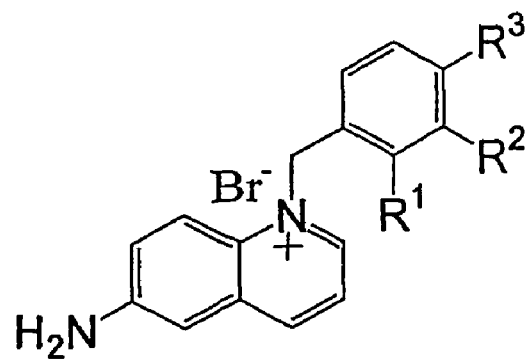
FIG. 12 shows the molecular structure of ortho-, meta-, and para-BAQBA probes and the control compound BAQ, which does not contain the boronic acid moiety.

Molecular structure of ortho-, meta-, and para-BAQBA probes and the control compound BAQ, which does not contain the boronic acid moiety are shown in FIG. 12.

All solution absorption measurements were performed in a 4×1×1-cm quartz cuvette (Starna), using a Cary 50 spectrophotometer from Varian. Fluorescence spectra were similarly collected on a Varian Eclipse spectrofluorometer with solution optical densities less than 0.2 and $\lambda_{ex}$=358 nm. Stability, dissociation constants (KD), mean lifetime, intensity decay were determined as set forth in Example 1.

Figure 13:
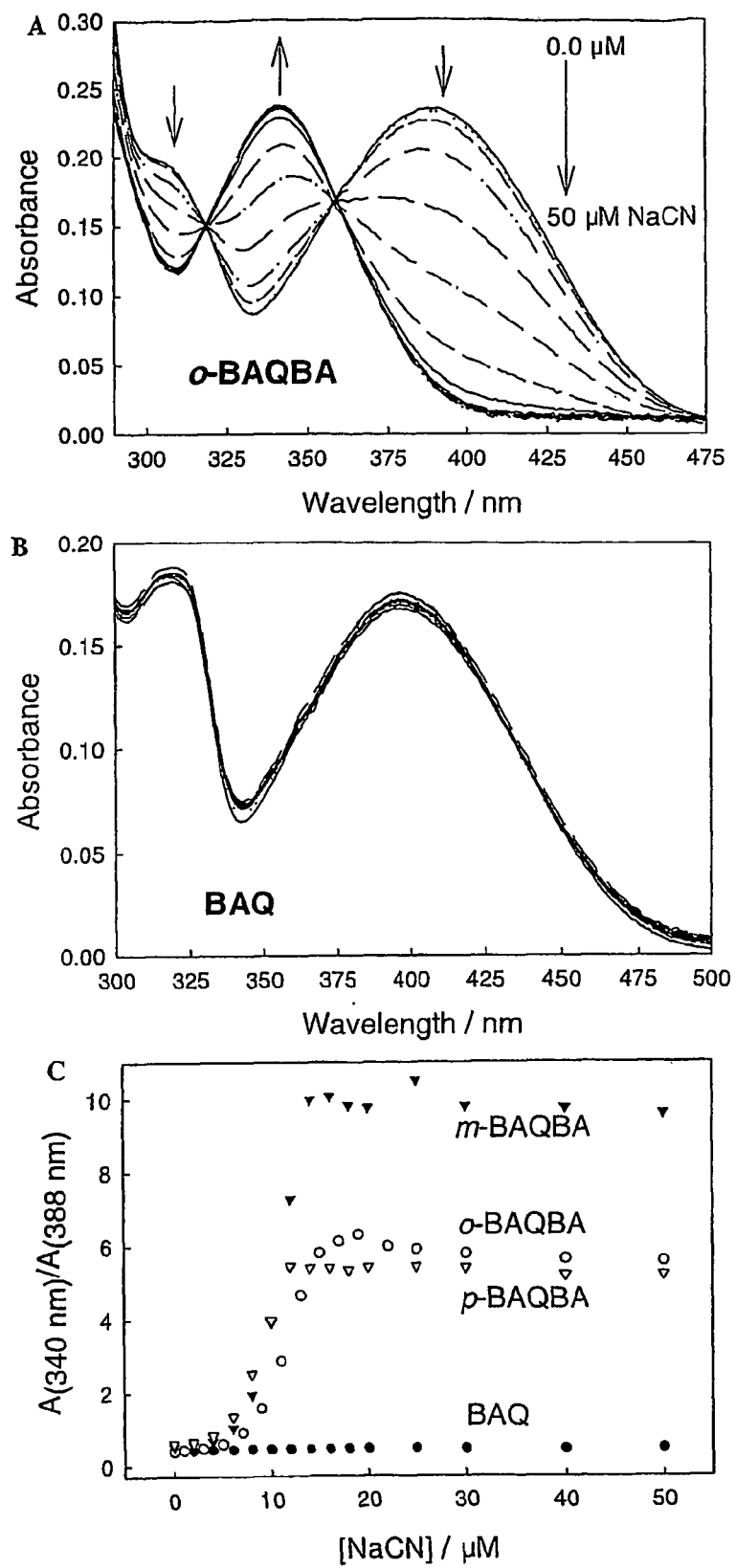
FIGS. 13A, B and C show the absorption spectrum of (A) o-BAQBA and (B) BAQ with increasing cyanide concentration and (C) the respective wavelength ratiometric plots based on the $A_{340}/A_{388}$-nm bands.

FIGS. 13A and B show the absorbance for both o-BAQBA and BAQ with increasing cyanide concentrations, respectively. As the cyanide concentration increases the absorption band at 388 nm decreases while the band at 340 nm increases. Notably, significant changes in both bands can be seen as the cyanide concentration is increased (FIG. 13A). As expected the absorption spectrum of BAQ is unchanged by the addition of cyanide, confirming expectations that the boronic acid moiety of BAQBA binds cyanide as depicted in FIG. 1 and that BAQ does not. To the best of our knowledge, the boronic acid group has not been reported to both bind and thus sense cyanide in this manner. All three BAQBA probes showed similar responses to cyanide. Subsequently, FIG. 13C shows the absorption wavelength ratiometric plots for all three BAQBA probes and BAQ based on the $A_{340}/A_{388}$g-nm bands. Interestingly, m-BAQBA shows a much stronger response with a greater dynamic sensing range than the other two ortho- and para-BAQBA probes.

The fluorescence emission of the BAQBA probes shows similar wavelength ratiometric behavior (FIG. 14A) where $\lambda_{ex}$=358 nm, i.e., at the isobestic point. As the cyanide concentration increases, a decrease in the 546-nm emission band was seen and a subsequent increase in the 450-nm band, which is attributed to the emission of the cyanide-bound complexed form. This ratiometric response can also be seen visually in FIG. 15. Interestingly, solutions of o-BAQBA showed useful color changes from green (Safe) to completely colorless (Danger) by the addition of 20 uM cyanide as shown in FIG. 15. This result strongly suggests the use of these BAQBA probes for cyanide determination <20 uM, which is important for physiological detection and safeguard. In contrast, BAQ shows very little change in fluorescence intensity (FIG. 14B), with no ratiometric behavior observed (FIG. 14C).

Figure 14:
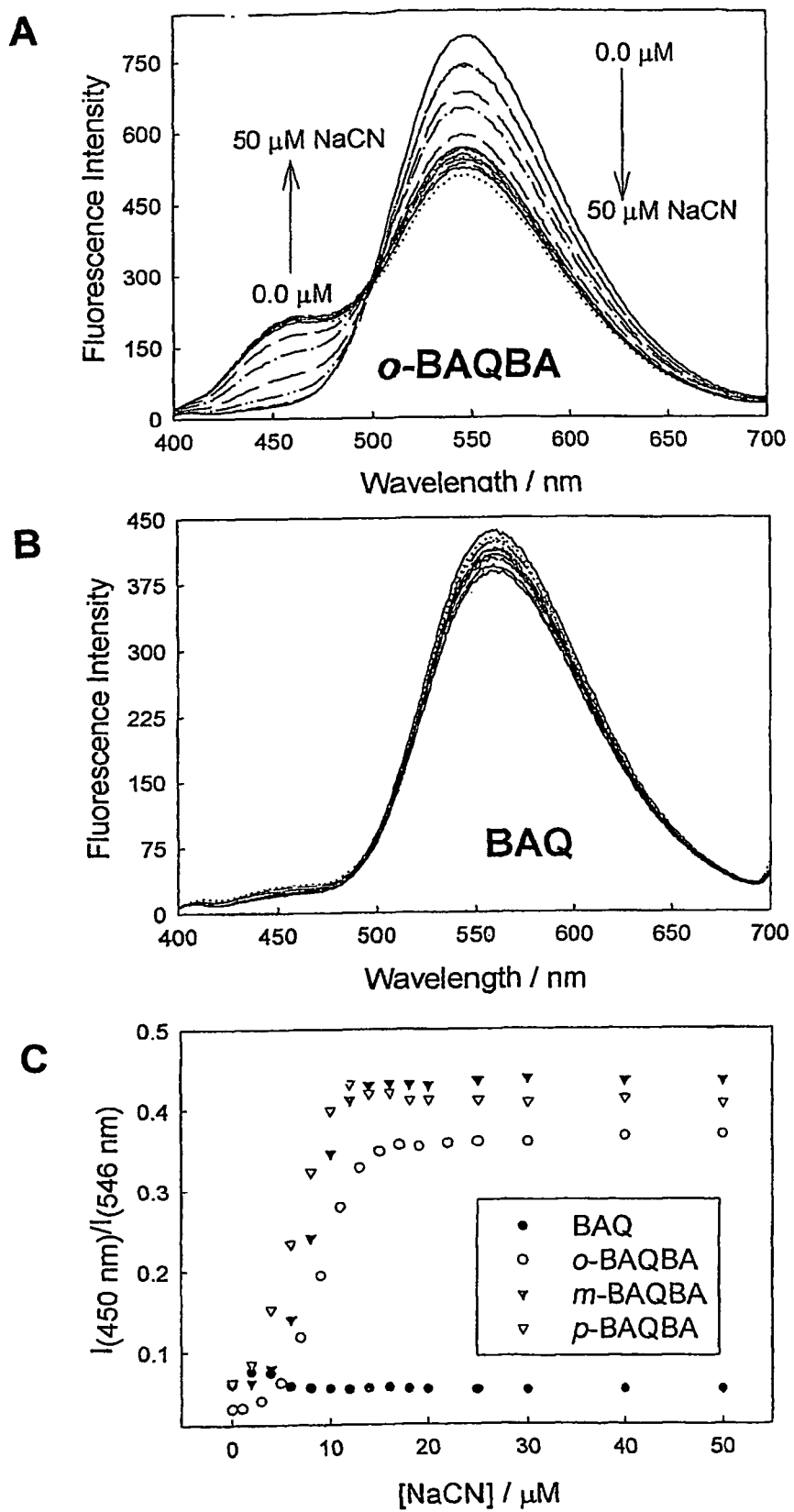
FIGS. 14A, B and C show the fluorescence emission spectra of (A) o-BAQBA and (B) BAQ with increasing cyanide concentration and (C) the respective wavelength ratiometric plots based on the $I_{450}/I_{546}$-nm bands.
Figure 15:
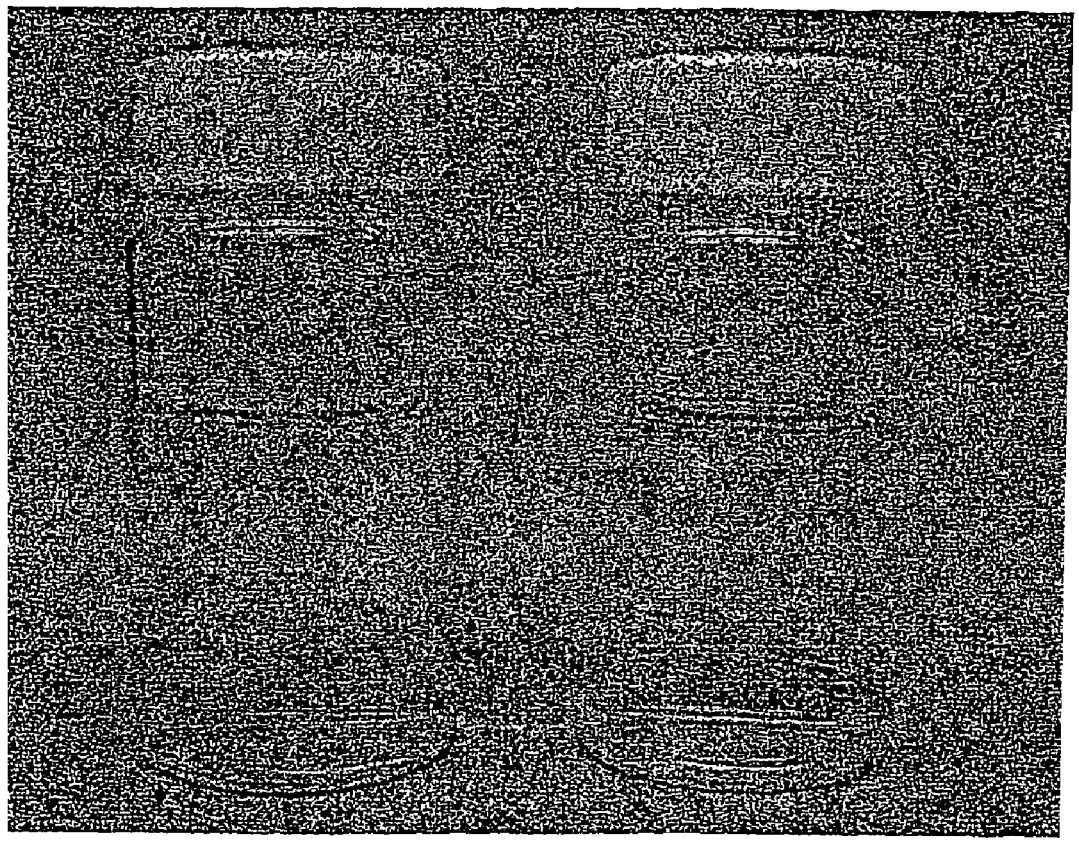
FIG. 15 shows a photograph of two vials containing equal concentrations of o-BAQBA and both 0 and 10 uM NaCN, left vial, green color (safe) and right vial, clear (danger), respectively. Very similar findings were observed for all three boronic acid probes.

The fluorescence emission wavelength ratiometric response was constructed and shown in FIG. 14C, wherein all three BAQBA probes having a similar response to aqueous cyanide. By comparing FIG. 13C and FIG. 14C, a greater change is observed for the ratiometric absorption measurements, reflecting the difference in extinction coefficients and quantum yields of the $CN^-$ unbound and bound forms, respectively. Using Equation 1 and the data as set forth in FIG. 14C, the cyanide binding constants were determined for the ortho-, meta-, and para-boronic acid probes to be 0.12, 0.17, and 0.14 $uM^{-3}$, noting the units $uM^{-3}$ or $mol^{-3}$ $dm^9$.

Figure 16:
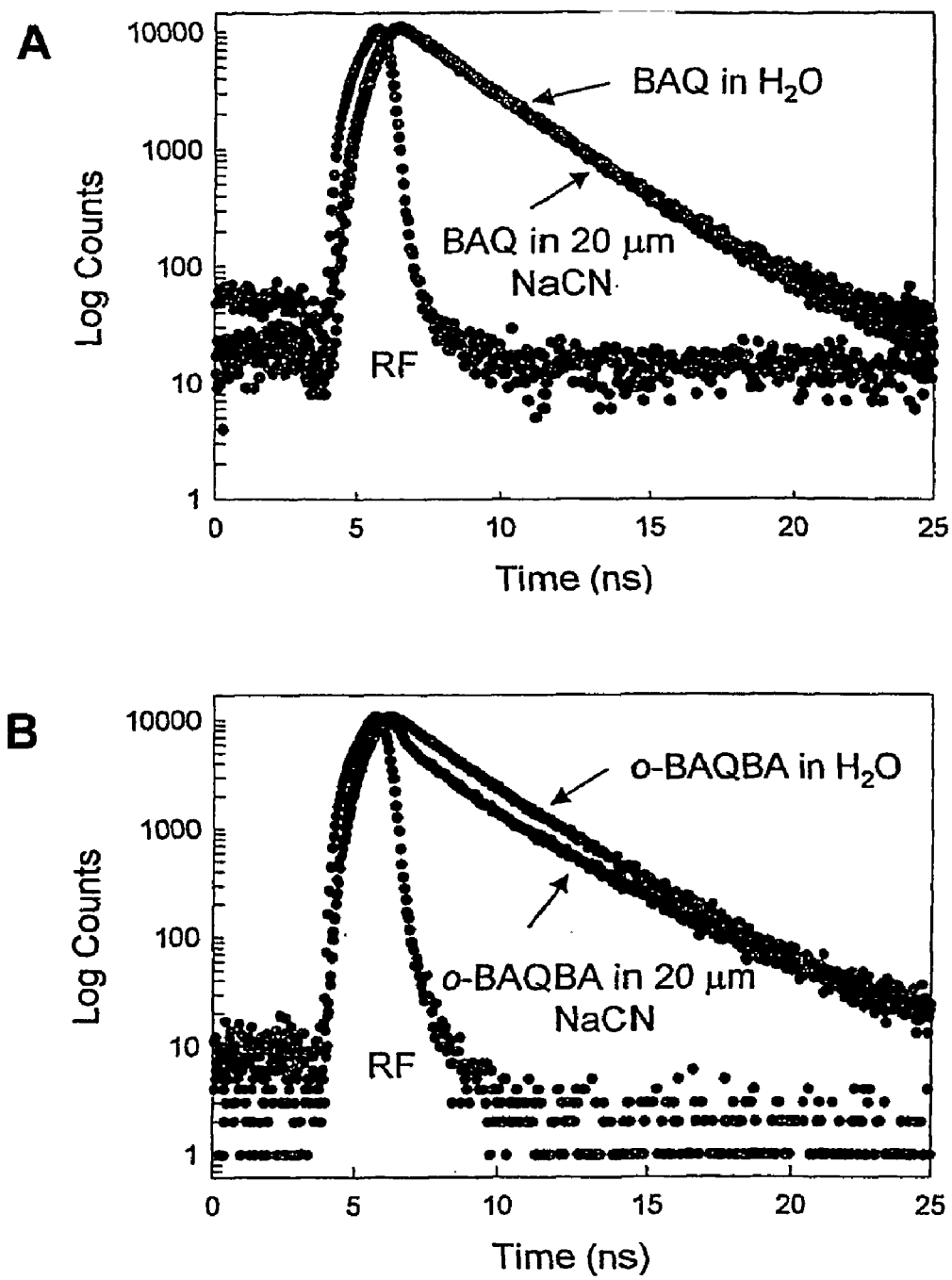
FIGS. 16A and B show the intensity decays for (A) BAQ and (B) o-BAQBA in the absence and presence of aqueous cyanide. RF, instrumental response function, fwhm ≈1.1 ns. Similar results were also obtained for m- and p-BAQBA.

The lifetimes of the probes were measured in the absence and presence of cyanide, using the well-known TCSPC technique [31] to investigate the possibility of fluorescence lifetime ratiometric sensing (see FIGS. 16A and B and data of Table 4 shown in FIG. 17). BAQ was found to be monoexponential in Millipore water with a lifetime of ≈2.49 ns, unperturbed by the addition of sodium cyanide and further strengthening the proposed cyanide binding mechanism as shown in FIG. 1. This can be clearly seen in FIG. 16A where the addition of 20 uM NaCN does not perturb the intensity decay of BAQ.

The lifetimes of the two emission bands of the BAQBA probes were measured separately, using both a 380-nm long-pass filter and a 550-nm±10 interference filter. Table 4 (FIG. 17) shows that the lifetimes of the emission band at 550 nm is unaltered by aqueous NaCN, where both the mean and the amplitude weighted lifetimes remain approximately constant. However, when the lifetimes were determined through a 380-nm long-pass filter a short-lived component, <400 ps, becomes evident at high $CN^-$ concentrations as shown in Table 4, as a third component in the intensity decay. This can be seen visually in FIG. 16B and is in contrast to that observed for BAQ. This short-lived component was assigned to the lifetime of the $CN^-$ bound complex form of the o-BAQBA. While this short-lived species is measurable with a UV LED for excitation (fwhm ≈1.1 ns), it's ps lifetime prevents its practical use for ratiometric lifetime sensing [31, 32]. Similar results were found for all three BAQBA probes, with a longer lifetime component additionally observed for m-BAQBA.

The affinity of boronic acid for diols is well known. As such, the response of the BAQBA probes toward glucose and fructose was tested, and using Equation (1) the binding constants for o- and m- was determined to be 3.90 and 3.18 $mM^{-1}$ for glucose and 1.06 and 1.55 $mM^{-1}$ for fructose (data not shown; no data are available for p-BAQBA). Interestingly, the response for glucose was found to be higher than that for fructose, but all were significantly lower than that determined for cyanide. While it is difficult to make direct comparisons because the units are different, the relatively higher affinity for the cyanide anion suggests that monosaccharides, such as glucose and fructose, would not interfere in cyanide measurements.

Figure 18:
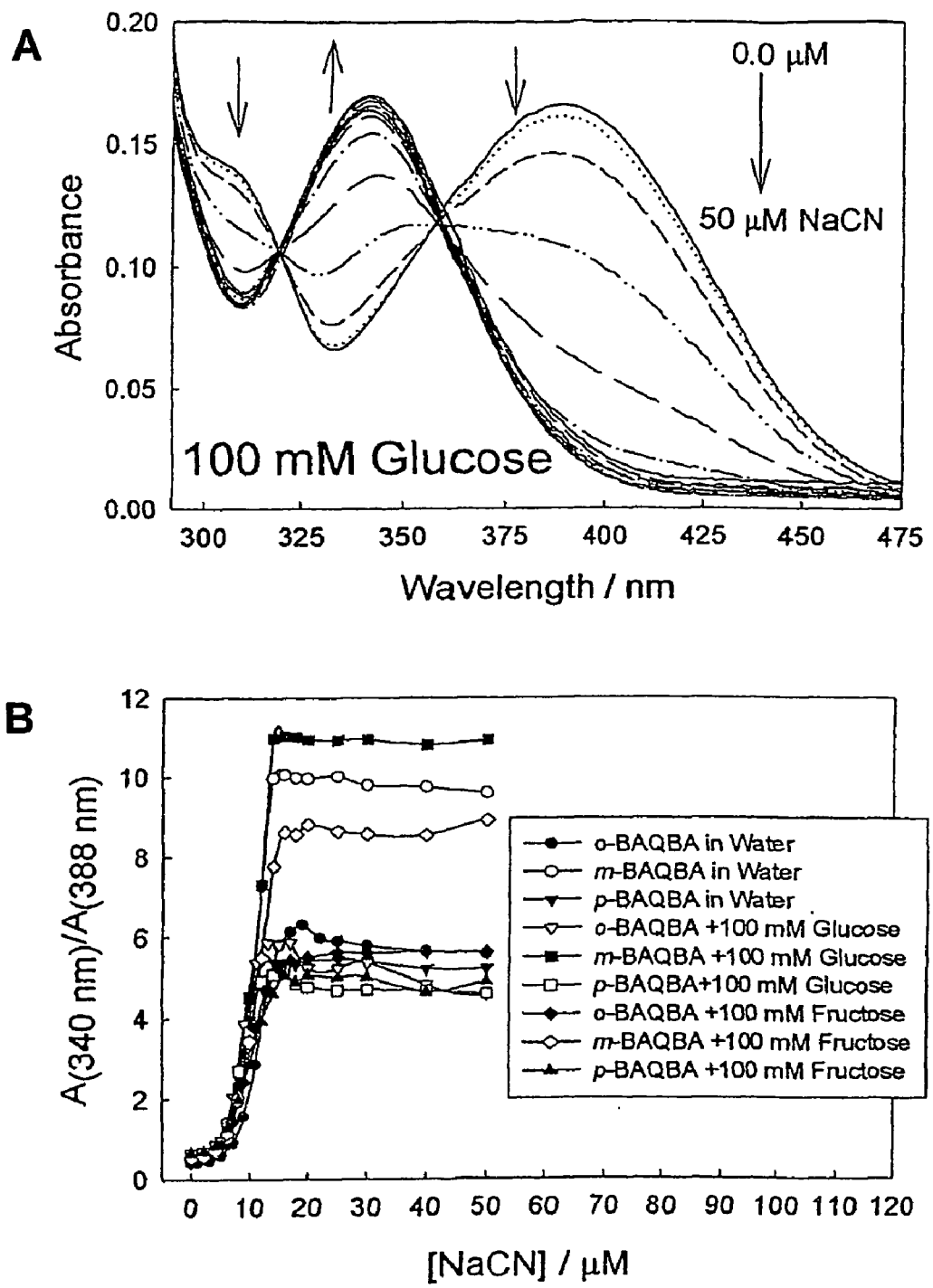
FIGS. 18A and B show the absorption spectra of o-BAQBA with increasing cyanide concentrations, in the presence of 100 mM glucose (A), and the respective ratiometric plots ($A_{340}/A_{388}$-nm bands) for o-, m-, and p-BAQBA in the presence of either 100 mM glucose or fructose, for increasing cyanide concentrations (B).
Figure 19:
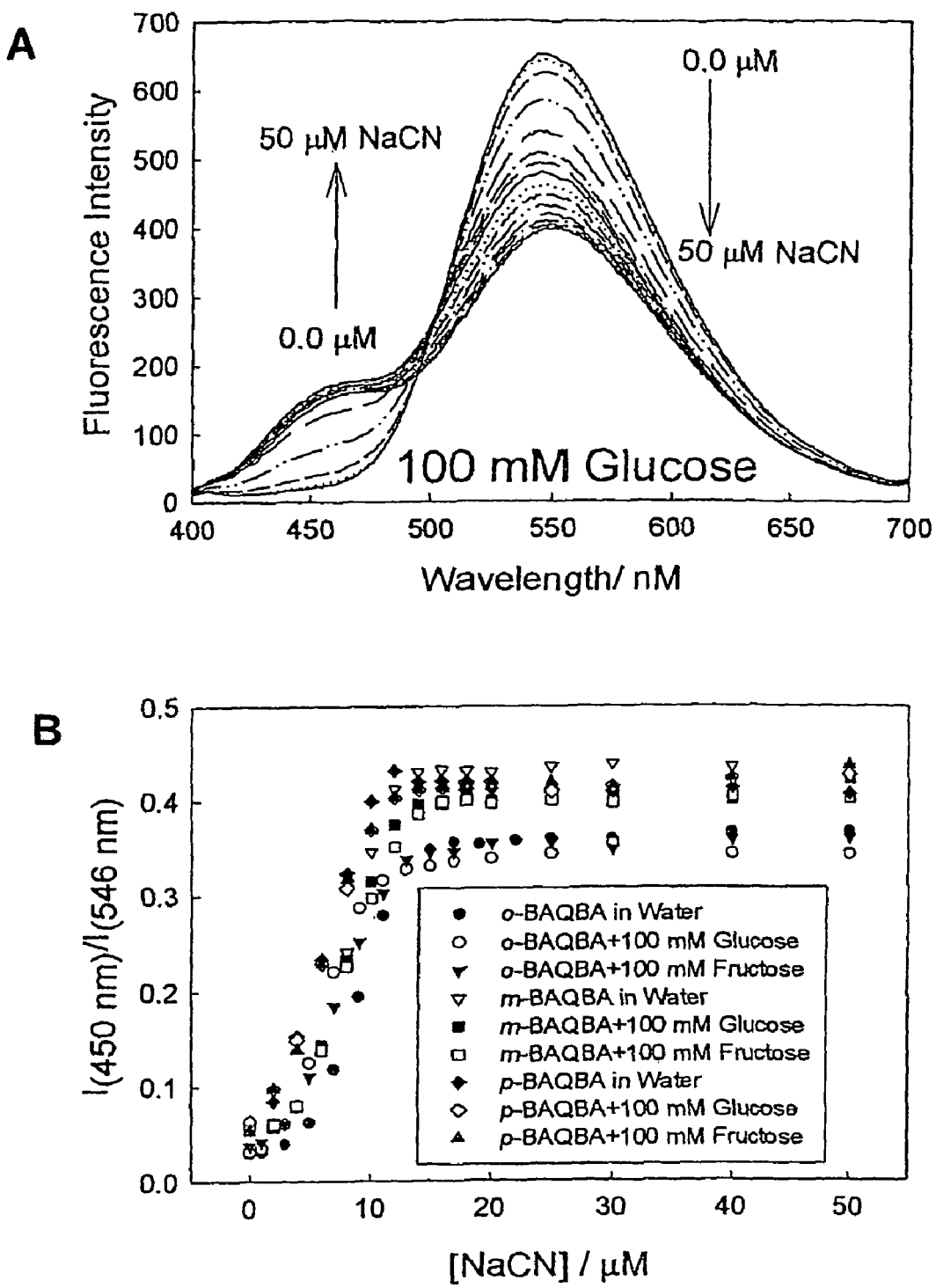
FIGS. 19A and B show the emission spectra of o-BAQBA with increasing cyanide concentrations, in the presence of 100 mM glucose, $\lambda_{ex}$=358 nm (A), and the respective ratiometric plots ($I_{450}/I_{546}$-nm bands) for o-, m-, and p-BAQBA in the presence of either 100 mM glucose or fructose, for increasing cyanide concentrations (B).

Subsequently, the absorption and emission wavelength ratiometric response were measured in the presence of a constant background of 100 mM glucose or fructose (FIGS. 18 and 19, respectively). Interestingly, the presence of the sugars did not interfere with the cyanide measurements, similar results being determined for cyanide in both the absence (just in water) and the presence of either 100 mM glucose or fructose. The relatively higher binding affinity for cyanide by m-BAQBA was not surprising, given similar reports for other meta-positioned boronic acid groups on other fluorophores [38].

Figure 20:
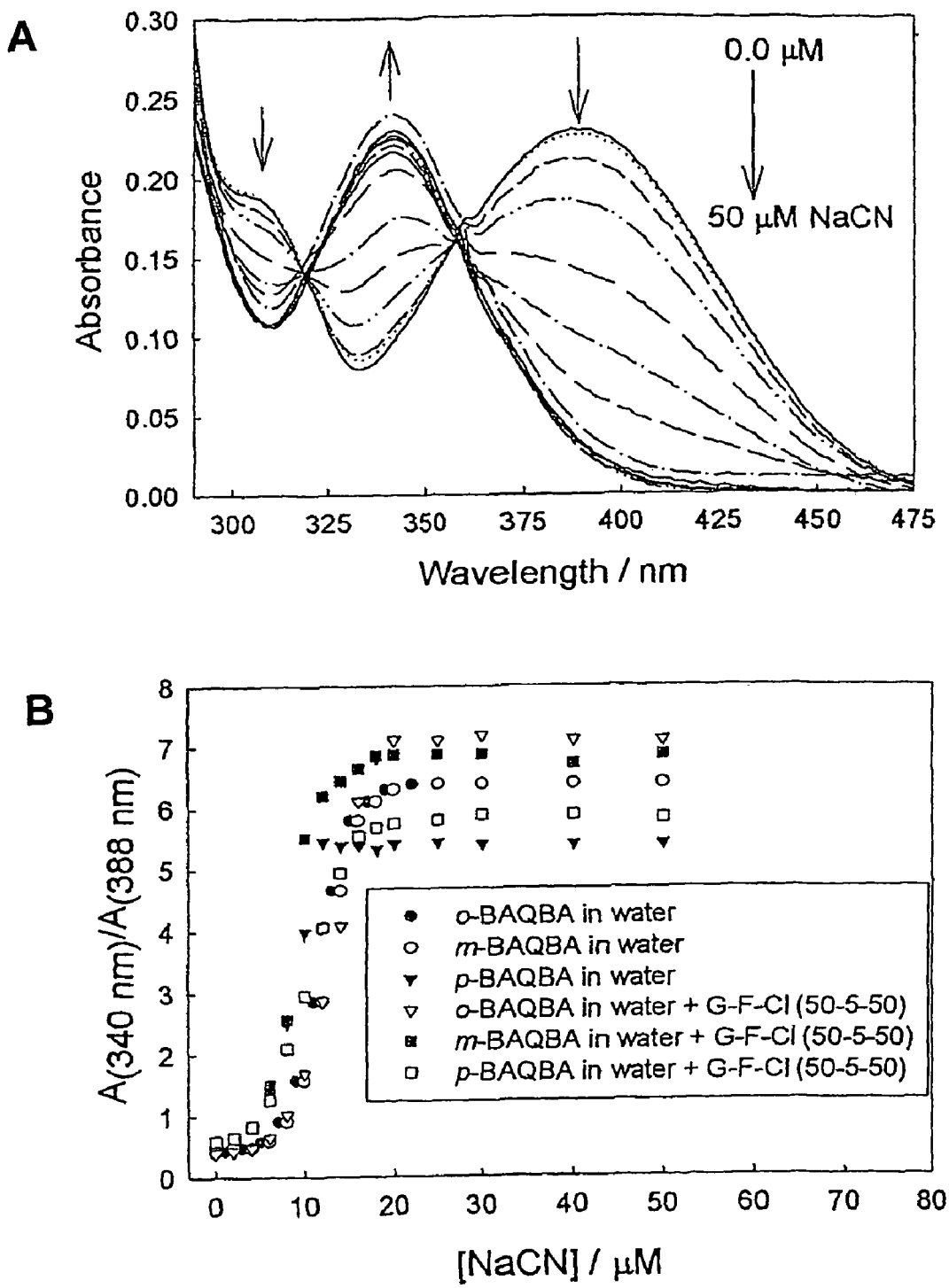
FIGS. 20A and B show the absorption spectra of o-BAQBA with increasing cyanide concentrations, in the presence of 50 mM glucose, 5 mM fructose, and 50 mM chloride, (A), and the respective ratiometric plots ($A_{340}/A_{388}$-nm bands) for o-, m-, and PBAQBA in the presence of the same physiological-like background cocktail with increasing cyanide concentrations (B).
Figure 21:
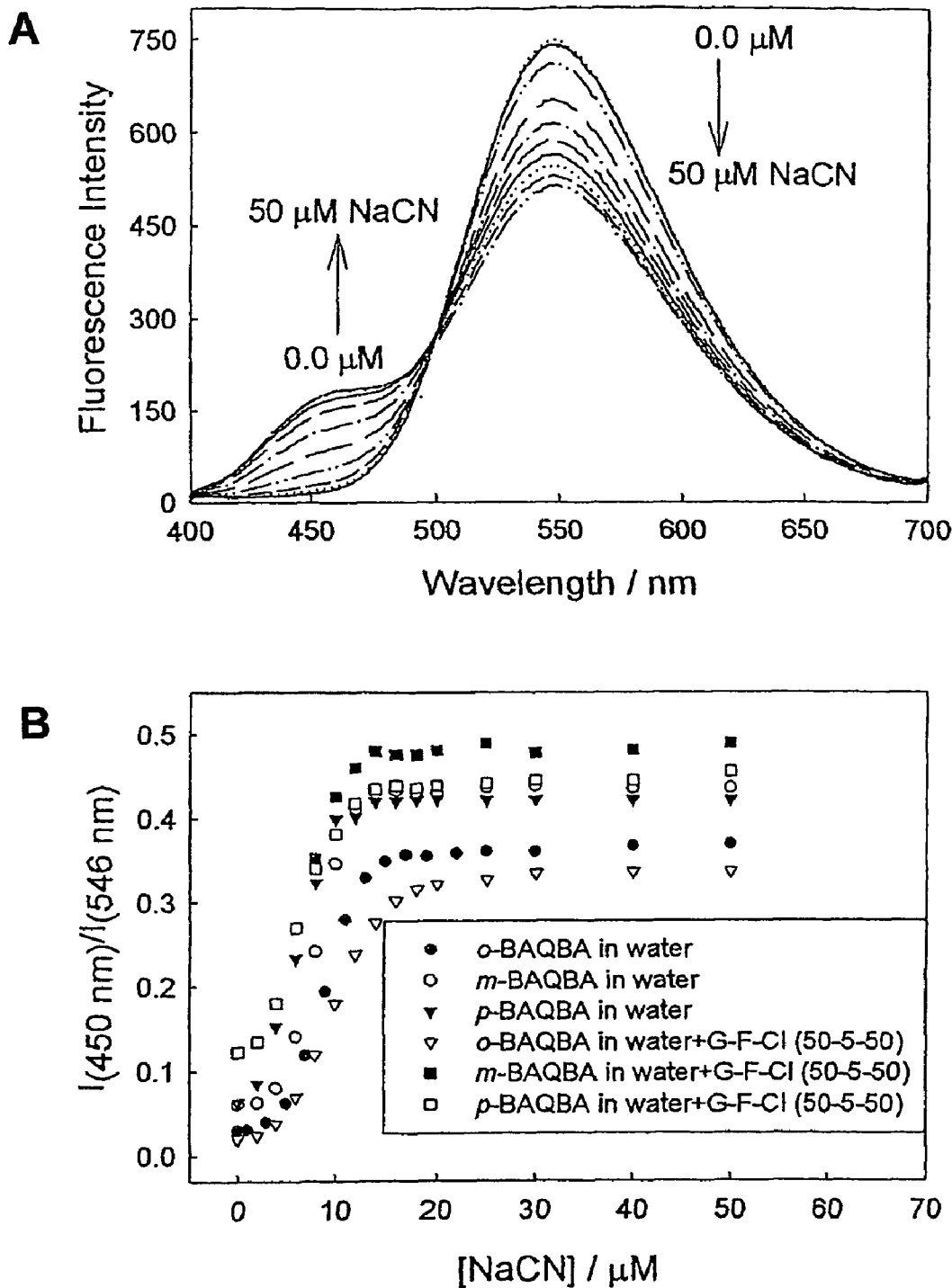
FIGS. 21A and B show the emission spectra of o-BAQBA with increasing cyanide concentrations, in the presence of 50 mM glucose, 5 mM fructose, and 50 mM chloride, $\lambda_{ex}$=358 nm (A), and the respective ratiometric plots ($I_{450}/I_{546}$-nm bands) for o-, m-, and p-BAQBA in the presence of the same physiological-like background cocktail, for increasing cyanide concentrations (B).

The quenching of the BAQBA probes by aqueous chloride was tested, which is known to quench some quinolinium fluorescence [33]. The Stern-Volmer constants were determined, $K_{SV}$[33], for o-, m-, and p-BAQBA all to be ≈1.0 $M^{-1}$, in essence displaying only a very weak quenching [33]. This was surprising as many quinolinium-type fluorophores have much more notable responses toward chloride and are therefore used as chloride probes [32 and 33]. The absorption and the emission wavelength ratiometric responses of the BAQBA probes were tested toward cyanide in the presence of a physiological-like cocktail of 50 mM glucose, 50 mM chloride, and 5 mM fructose (FIGS. 20 and 21, respectively). The results show that the response toward cyanide is maintained and that these potential physiological interferences do not perturb the dynamic range for cyanide sensing as shown in FIGS. 20B and 21B.

The relatively higher binding constant for cyanide than for glucose and fructose and the fact that chloride does not quench BAQBA florescence strongly suggests the use of these probes for physiological cyanide determination and safeguard.

Example 3

To show the generic application of the boronic acid moiety to cyanide sensing, several different mechanisms were chosen, which have been previously used to induce spectral changes in the presence of sugar. In particular dyes were used that showed excited-state charge transfer (CT) [37, 36, 35 and 46], photo-induced electron transfer (PET) [49] and a probe based on a resonance interaction (RI) [47]. The fluorescent probes, as shown in FIG. 22, were prepared as previously reported [37, 36, 35, 47, 48 and 49].

Figure 22:
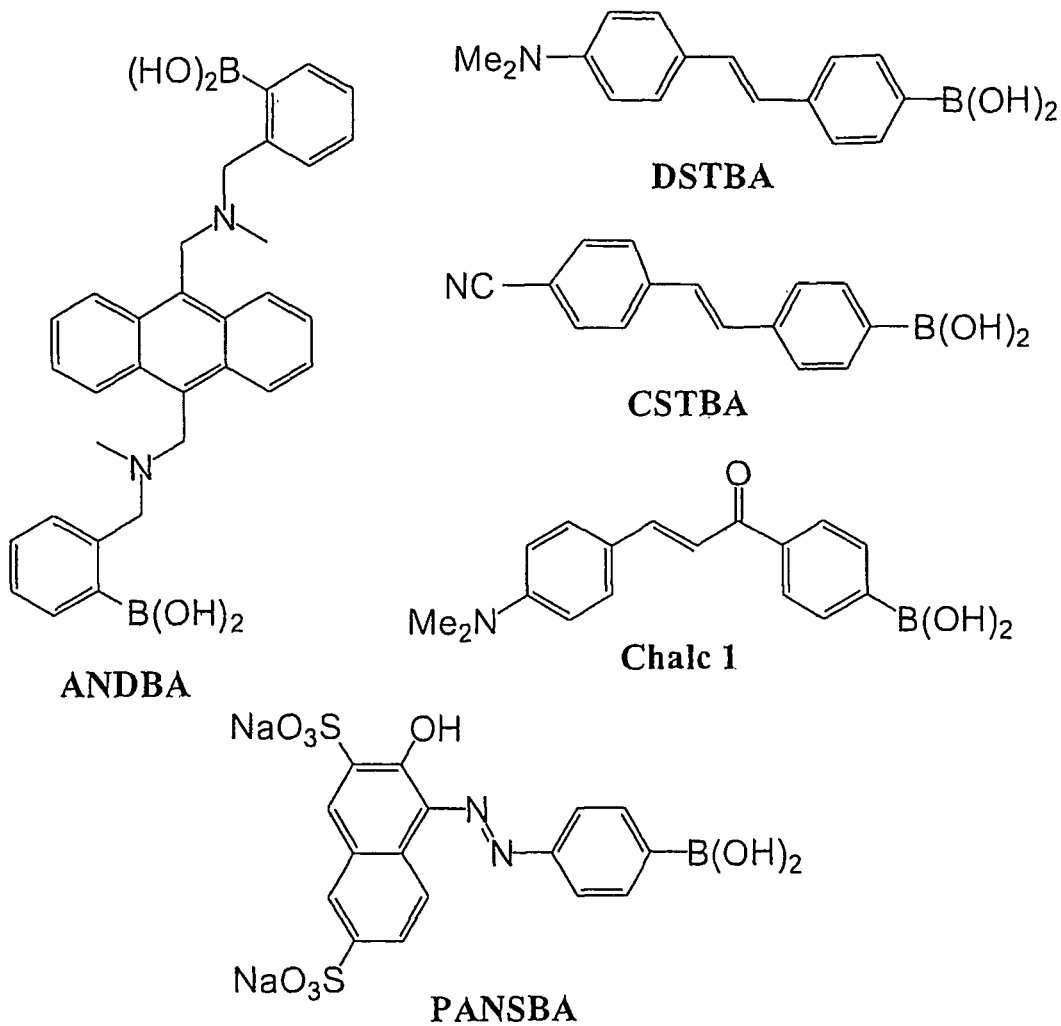
FIG. 22 shows the molecular structures of probes screened for their interactions with aqueous cyanide. DSTBA, 4'-dimethylaminostilbene-4-boronic acid; CSTBA, 4'-cyanostilbene-4-boronic acid; Chalc 1, 3-[4'(dimethylamino)phenyl]-1-4'-boronophenyl)-prop-2-en-1-one; ANDBA, 9,10-bis[[N-methyl-N-(o-boronobenzyl)amino]methyl]-anthracene; PANSBA, 1-(4-boronophenylazo)-2-hydroxy-3,6-naphthalenedisulfonic acid disodium salt.

FIG. 22 shows two stilbene derivatives that contain the boronic acid moiety. DSTBA, 4'-dimethylaminostilbene-4-boronic acid, which combines the electron-donating dimethylamino group with the electron-withdrawing boronic acid group and CSTBA, 4'-cyanostilbene-4-boronic acid, which combines the electron-withdrawing cyano group with boronic acid.

Figure 23:
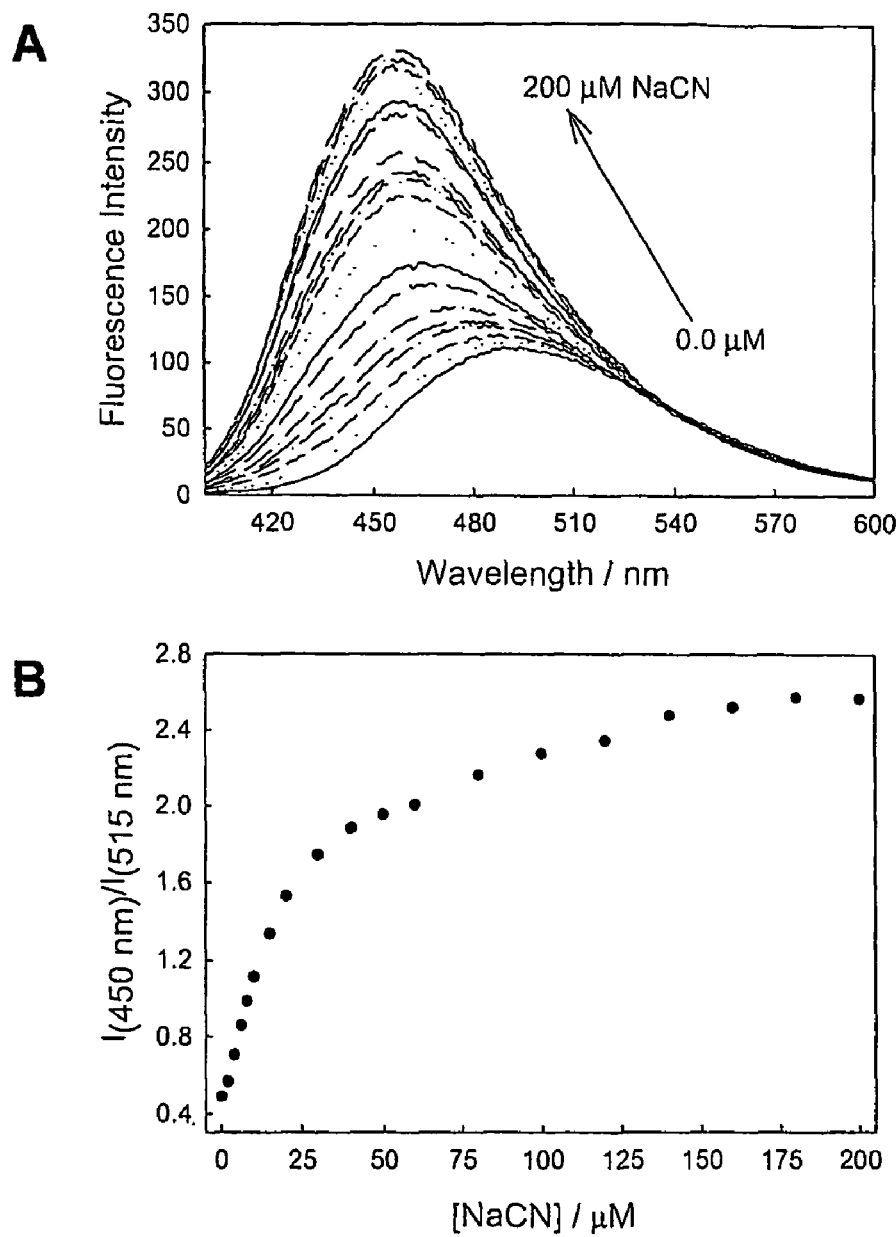
FIGS. 23A and B show the fluorescence emission spectra of DSTBA with increasing concentrations of aqueous cyanide (A) and the respective ratiometric plot using the intensities at 450 and 515 nm (B).

FIG. 23A shows the fluorescence emission spectra of DSTBA with increasing concentrations of aqueous cyanide. The emission spectra show a hypsochromic shift of about 40 nm and an increase in fluorescence intensity as the concentration of cyanide is increased. These dramatic and useful changes were also observed with monosaccharides [36] and can be explained by the loss of the electron-withdrawing property of the boronic acid group following the formation of the anion cyanide bound form, $R-B-CN^-)_3$, as shown in FIG. 1. The emission wavelength ratiometric plots were constructed based on the 450 and 515 nm intensity values (FIG. 23B) where an almost linear response towards aqueous cyanide can be observed up to physiological safeguard limits, <20 μM. Using Equation 1 as set forth in Example 1, the dissociation constant was estimated to be ≈27 μM³ as shown below in Table 5, as compared to a value of 98 mM for D-glucose and 2.5 mM for D-fructose, as previously reported in reference [36].

TABLE 5

Dissociation constants of the probes with cyanide in water

| Probe | $K_D$ (μM³) |
|---|---|
| ANDBA | 3.90 |
| DSTBA | 27.20 |
| CSTBA | 6.90 |
| Chalc 1 | 3.60 |
| PANSBA | 7.95 |

Figure 24:
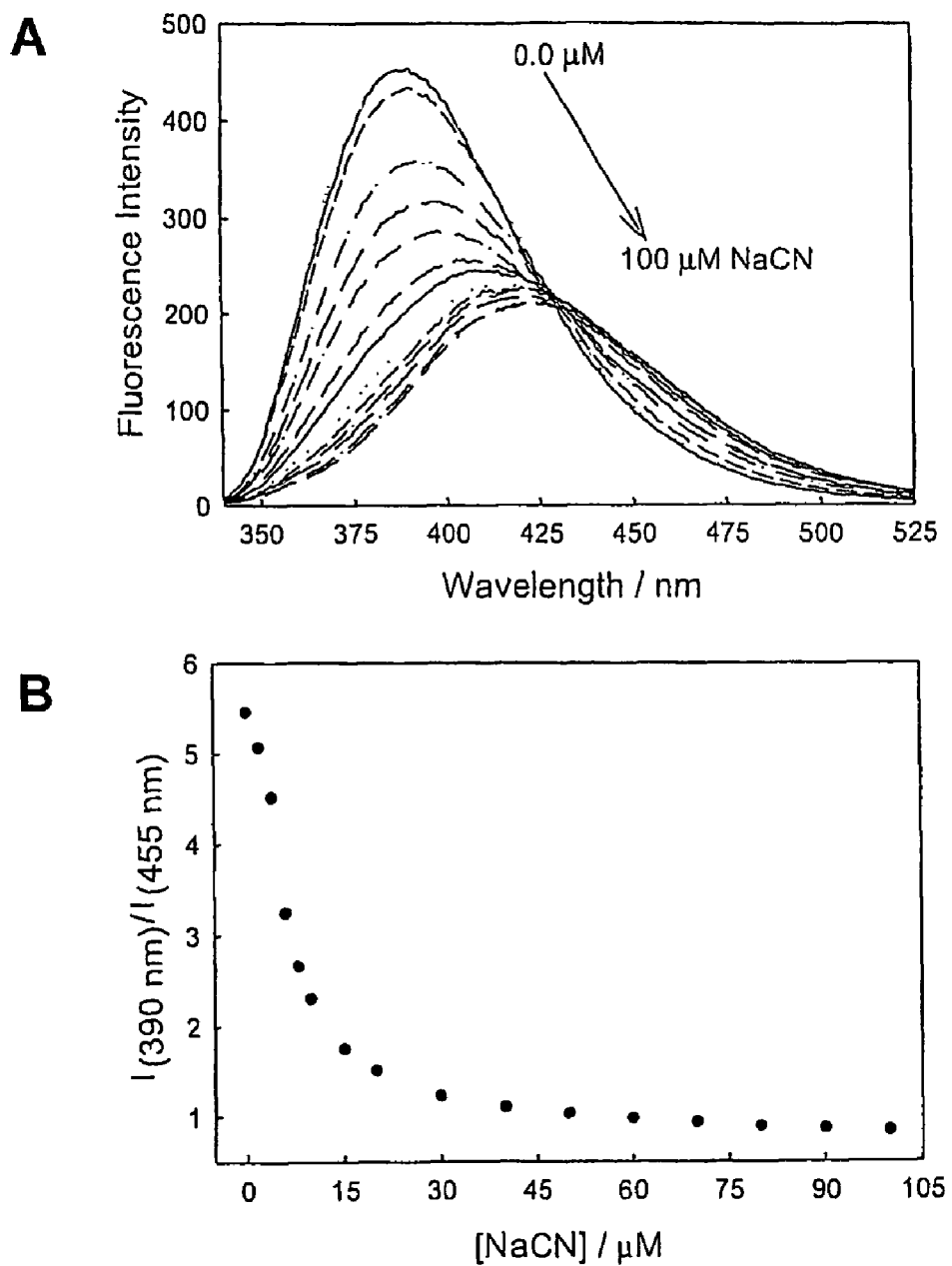
FIGS. 24A and B show the fluorescence emission spectra of CSTBA with increasing concentrations of aqueous cyanide (A), and the respective ratiometric plot using the intensities at 390 and 455 nm (B).

The CSTBA stilbene derivative possesses two electron-withdrawing groups. In the presence of cyanide, a 35 nm bathochromic shift, accompanied by a decrease in fluorescence intensity is observed as shown in FIG. 24A. This is opposite to that observed for DSTBA but similar to that reported for a sugar response [36, 34]. This difference in behavior can likewise be attributed to an excited CT state present for the anionic form of CSTBA, where no CT states are observed for the neutral form of the boronic acid group [36]. This suggests that the anionic form of the boronic acid group can act as an electron-donating group. Similarly for DSTBA, the emission wavelength ratiometric plot was constructed based on the 390 and 455 nm emission intensity values as shown in FIG. 24B, where up to a 6-fold change in $I_{390}/I_{455}$ can be observed in the cyanide physiological safeguard region.

Figure 25:
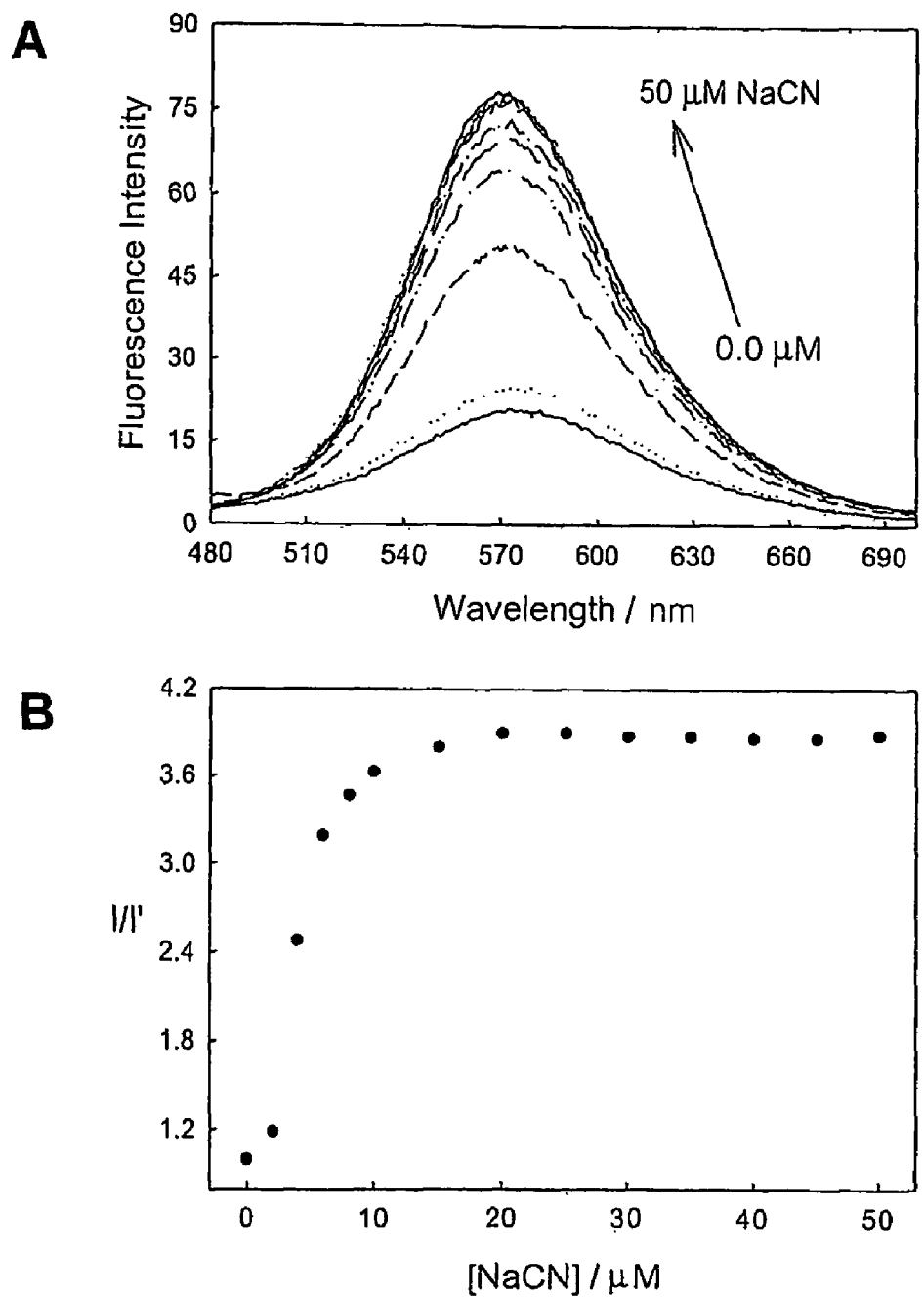
FIGS. 25A and B show the fluorescence emission spectra of Chalc 1 with increasing concentrations of aqueous cyanide (A), and the respective ratiometric type plot using the initial fluorescence intensity, I', at 570 nm in the absence of cyanide, and in the presence of increasing cyanide concentrations, I (B).

Chalcone derivatives, unlike the stilbenes, have the advantage of much longer wavelength emission, allowing their potential use with cheaper and longer wavelength laser or light emitting diode sources. For Chalc 1, the boronic acid group does not produce resonance forms with the electron-donating amino group [45, 36]. The CT occurs between the dimethylamino group (electron-donating group) and the carbonyl group (electron-withdrawing group). Upon cyanide binding to the boronic acid group, a change in the electronic properties of the boronic acid group, directly leads to a change in the electronic density of the acetophenone moiety, noting that the boronic acid group is in resonance with the carbonyl group. The spectral changes observed in FIG. 25A were very similar to those obtained with sugar [36], further confirming the cyanide complexation interaction. Additionally, FIG. 25B shows the fluorescence intensity of Chalc 1 as a function of increasing cyanide concentration, normalized by the initial intensity in the absence of cyanide. An approximate 3.5-fold intensity change is observed with the addition of 10 μM CN⁻, with a dissociation constant of 3.6 μM³.

Photo-induced electron transfer is often used as a mechanism for fluorescence quenching in the development of many sensors [49]. The quenching is due to an electron rich amino group near the fluorophore. When the analyte of choice binds to the PET probe, then this new interaction with the nitrogen's lone pair dominates, removing the quenching, with an increase in fluorescence intensity observed. For glucose sensors, the mechanism is slightly different. In this case, changes in the acidity of the boron atom and the nitrogen atom in the presence of glucose are responsible for the intensity changes.

Figure 26:
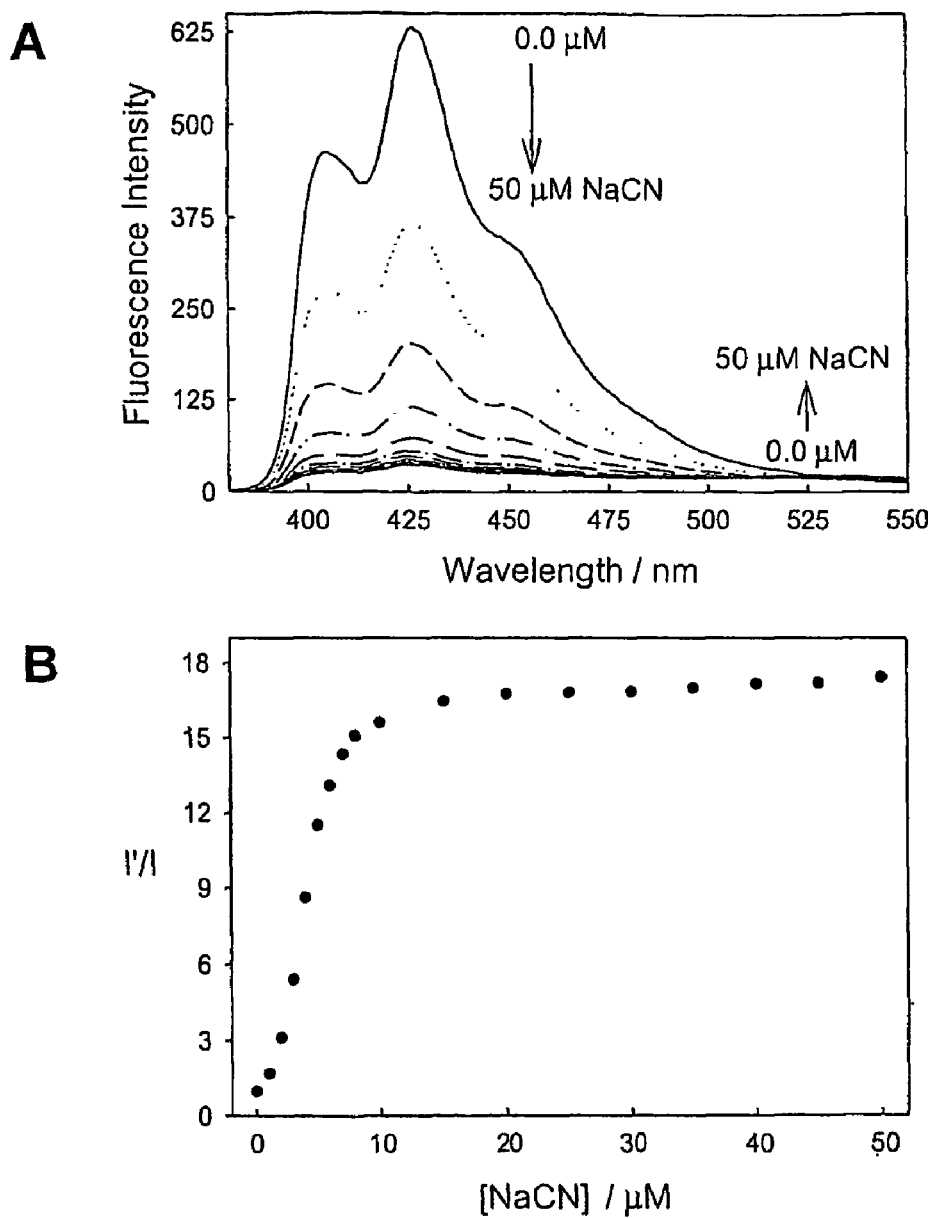
FIGS. 26A and B show the fluorescence emission spectra of ANDBA with increasing concentrations of aqueous cyanide (A) and the respective ratiometric type plot using the initial fluorescence intensity, I', at 425 nm in the absence of cyanide, and in the presence of increasing cyanide concentrations, I (B).

FIG. 26A shows the interaction of an anthracene derivative, ANDBA, containing amino and phenyl boronic acid groups, with aqueous cyanide. This PET probe has been well characterized with regard to monosaccharides. The addition of 10 μM cyanide almost completely quenches the ANDBA fluorescence, with a ≈15-fold, almost linear change in fluorescence intensity observed at 425 nm. This remarkable dynamic quenching range is most attractive here for physiological cyanide safeguard monitoring. In addition, ANDBA has been reported as a suitable fluorescence lifetime probe for glucose [49], which suggests its analogous use as a lifetime probe for cyanide. It is widely known that lifetime based sensing is preferred, as compared to intensity based sensing [31, 32], as fluorescence lifetimes are generally independent of the probe concentration and intensity of the fluorescence signal, as well as fluctuations in the excitation source.

Figure 27:
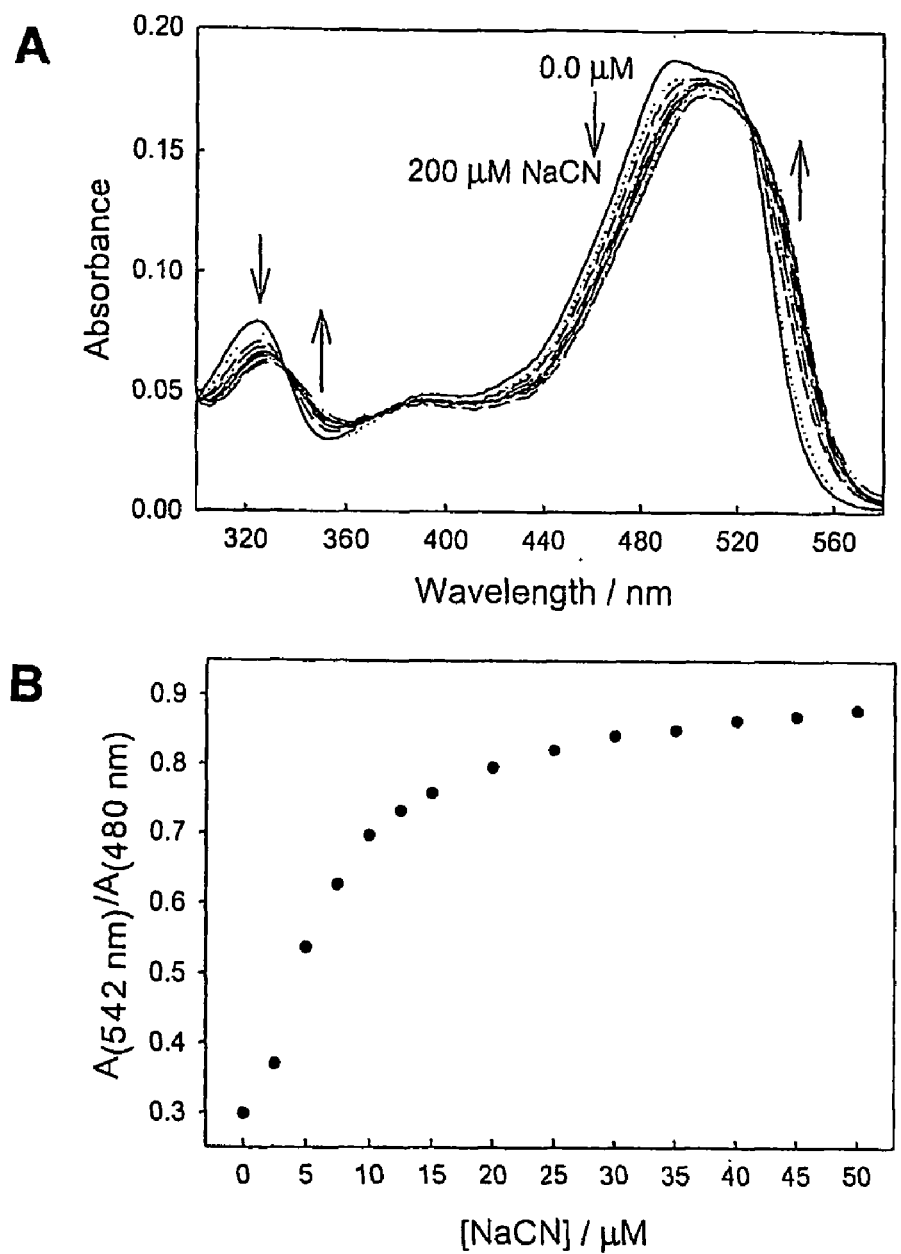
FIGS. 27A and B show the absorption spectra of PANSBA with increasing concentrations of aqueous cyanide (A) and the respective ratiometric plot using the intensities at 542 and 480 nm (B).
Figure 28:
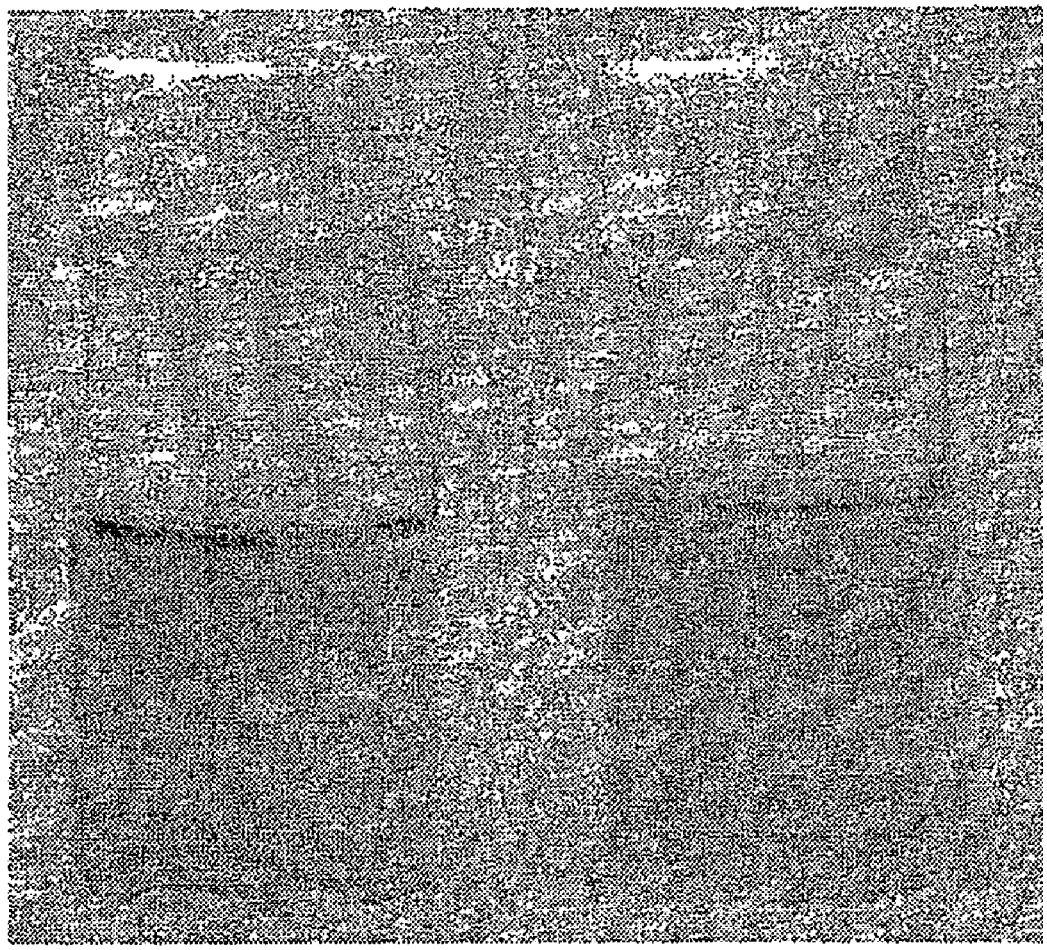
FIG. 28 shows a photograph of two vials containing equal concentrations of PANSBA with both 0 and 50 μM NaCN (left vial orange color (Safe) and right vial pink color (Danger), respectively).

Finally to assess the utility of boronic acid containing fluorophores for cyanide sensing, the use of azo-type dyes was considered which have been reported as being ideal "Color Chemosensors" for monosaccharides [47]. Again, a change in the electronic properties of the boronic acid between its neutral form (no cyanide) and anionic form (with cyanide) accounts for the spectral changes observed. FIG. 27A shows the changes in absorption spectra for increasing cyanide concentrations, where the small absorption changes are enough to be detected visually as shown in FIG. 28. A colorimetric type response towards aqueous cyanide is visible as the solution in the left vial orange (Safe) changes to pink (Danger). While the absorption ratiometric plot shown in FIG. 27B shows a relatively smaller dynamic sensing range as compared to others discussed here, the utility of this probe clearly lies in its visual response. It should be noted that the color change is thought to be due to the conformational change of the boron atom between its neutral and anionic forms, i.e., the boronic acid group is an electron-deficient Lewis Acid having an sp²-hybridized boron atom and a triangular conformation, while the anionic form is an electron rich sp³-boron atom with a tetrahedral geometry. Despite the changes between the electron-withdrawing and donating properties of the boronic acid group, the effect of intramolecular charge transfer is thought to be weak [47].

Given that cyanide induces spectral changes, it is concluded that cyanide complexation with boronic acid does not appear specific to just certain classes of fluorophores. This important finding suggests the widespread application of boronic acid containing fluorophores for cyanide sensing.

Abbreviations:
ANDBA, 9,10-bis[[N-methyl-N-(o-boronobenzyl)amino]methyl]-anthracene;
BA, boronic acid;
BAQ, N-benzyl-6-aminoquinolinium bromide;
o, m. p-BAQBA-N-(2, 3 or 4-boronobenzyl)-6-aminoquinolinium bromide.
o,m,p-BMOQBA-N-2, 3 or 4-boronobenzyl)-6-methoxyquinolinium bromide
BMOQ-N-benzyl-6-methoxyquinolinium bromide
o,m,p-BMQBA-N-(2,3,4-boronobenzyl)-8-methylquinolinium bromide
BMQ-N-benzyl-6-methylquinolinium bromide
BAF and BAFs, boronic acid containing fluorophore/s;
CSTBA, 4'-cyanostilbene-4-boronic acid;
CT, charge transfer;
Chalc 1,3-[4'(dimethylamino)phenyl]-1-(4'-boronophenyl)-prop-2-en-1-one;
DSTBA, 4'-dimethylaminostilbene-4-boronic acid;
GI tract, gastrointestinal tract;
$K_{SV}$-Stern-Volmer quenching constant
LD-Laser Diode
$LD_{50}$-Lethal dose to 50% of the population
LED-Light Emitting Diode
PANSBA, 1-(4-boronophenylazo)-2-hydroxy-3,6-naphthalenedisulfonic acid disodium salt;
PET, photo-induced electron transfer
TCSPC-Time-Correlated Single Photon Counting

REFERENCES

All references cited herein are hereby incorporated by reference herein for all purposes.

[1] S. I. Baskin and T. G. Brewer, In Medical Aspects of Chemical and Biological Warfare, Eds. F. Sidell, E. T Takafuji and D. R. Franz, TMM publications, Washington, 1997, Chapter 10, p. 271-286 and references cited therein.
[2] J. S. Lang, D. Mullin, C. Fenyvesi, R. Rosenberg and J. Barnes, *US News & World Report*, Nov. 10 (1986) 29.
[3] Medical expert reports use of chemical weapons in Iran-Iraq war, UN Chronicle 22 (1985) 24-26.
[4] A. Ishii, H. Seno, K. Watanabe-Suzuki, 0. Suzuki and T Kumazawa, *Anal. Chem.*, 70(22) (1998)4873-4876.
[5] F. Moriva and Y. Hashimoto, *J. For. Sci.*, 46(6) (2001) 1421-1425.
[6] C. J Clark, D. Campbell and W. H. Reld, *Lancet.*, (1981) 1332-1335.
[7] O. Warburg, Hoppe-Seyler's, *Z Physiol Chem.*, 76 (1911) 331-346.
[8] D. Kellin, *Proc. R. Soc Lond. B. Biol. Sci.*, 104 (1929) 206-251.
[9] F. J. Baud, P. Barriot, and V. Toffis, *N. Engl. J. Med.*, 325 (1991)1761-1766.
[10] C. Giuriati, S. Cavalli, A. Gomi, D. Badocco and P. Pastore, *J. Chromato. A*, 1023(2004) 105-112.
[11] H. P. Beck, B. Zhang and A. Bordeanu, *Anal. Lett.*, 36 (2003)2211-2228.
[12] M. T. Fernandez-Arguelles, J. M. C. Costa-Fernandez, R Pereiro and A. Sanz-Medel, *Anal. Chim. Acta.*, 491(2003) 27-35.
[13] B. Deep, N. Balasubramanian and K. S. Nagaraja, *Anal. Lett.*, 36 (2003) 2865-2874.
[14] J. D. Favero and M. Tubino, *Anal. Sci.*, 19(2003)1139-1143.
[15] J. V. Ros-Lis, R. Martinez-Manez and J. Soto, *Chem. Commun.*, (2002) 2248-2249.
[16] K Cho, Y. S Jang, M. S. Gong, K Kim and S. W. Joo, *Appl. Sectrosc.*, 56 (2002) 1147-1151.
[17] G. Drochioiu, *Anal. Bioanal. Chem.*, 372 (2002) 744-747.
[18] C. Hughes, F. Lehner, L. Dirikolu, D. Harkins, J. Boyles, K McDowell, T. Tobin, J. Crutchfield, M. Sebastian, L. Harrison and S. I. Baskin, *Toxicol. Mech. Methods*, 13 (2003)129-138.
[19] A. Ipatov, M. Ivanov, S. Makarychev-Mikhailov, V. Kolodnikov, A. Legin and Y. Vlasov, *Talanta*, 58 (2002) 1071-1076.
[20] M. Hashino, K. Nagashima, M. Kamaya and N. Nakano, *Bunseki Kagaku*, 52 (2003) 481-484.
[21] G. Drochioiu, *Talanta*, 56 (2002)1163-1165.
[22] A. Tracqui, J. S. Raul, A. Geraut, L. Berthelon and B. Ludes, *J. Anal. Toxicol.*, 26 (2002)144-148.
[23] B. Vallejo-Pecharroman and M.D. L. de Castro, *Analyst*, 127 (2002) 267-270.
[24] W. R. Premasiri, R. H. Clarke, S. Londhe and M. E. Womble, *J. Raman Spectrsc.*, 32 (2001) 919-922.
[25] D. E. Barnes, P. J. Wright, S. M. Graham and E. A. Jones-Watson, *Geostandards Newsletter—The Journal of Geostandards aid Geoanalysi*, 24 (2000)183-195.
[26] D. L. Recalde-Ruiz, E. Andres-Garcia and M. E. Daiz-Garcia, *Analyst*, 125 (2000) 2100-2105.
[27] D. L. Recalde-Ruiz, E. Andres-Garda and M. E. Daiz-Garcia, *Quimica Anal.*, 18(1999)111-113.
[28] T. Mansfeldt and H. Biemath, *Anal. Chim Acta.*, 406 (2000) 283-288.
[29] E. Nakamura and M. Yagi, *Bunseki Kagaku*, 49 (2000) 55-58.
[30] E. Miralles, R. Compano, M. Granados and M. D. Prat, *Anal. Chim. Act.*, 403 (2000)197-204.
[31] J. R. Lakowicz, Principles of Fluorescence Spectroscopy, 2nd Edition, Kluwer/Academic Plenum publishers, New York 1997.
[32] Z. Gryczynski, I. Gryczynski and J. R. Lakowicz, Fluorescence Sensing Methods, *Methods in Enzymology*, 360 (2002) 44-75.
[33] C. D. Geddes, *Meas. Sci. Technol.*, 12(9) (2001) R53-R88.
[34] R. Badugu, J. R. Lakowicz and C. D. Geddes, *Anal. Biochem.* R. Badugu, J. R. Lakowicz and C. D. Geddes, The non-invasive continuous monitoring of physiological glucose using a novel monosaccharide-sensing contact lens, *Anal Chem.*, 76 (2004) (3), 610-618.
[35] N. Dicesare and J. R. Lakowicz, *J. Phys. Chem. A*, 105(2001) 6834-6840.
[36] N. Dicesare and J. R. Lakowicz, *J. Biomedical Optics*, 7(4) (2002) 538-545.
[37] N. Dicesare and J. R. Lakowicz, *J. Photochem. Photobiol. A: Chem.*, 143 (2001) 39-47.
[38] N. DiCesare, D. P. Adhikari, J. J. Heynekamp, M. D. Heagy and J.R. Lakowicz, *J. Fluorescence*, 12(2) (2002) 147-154.
[39] R. Badugu, J. R. Lakowicz and C. D. Geddes, *Org. Lett.*,.
[40] R. Badugu, J. R. Lakowicz and C. D. Geddes, *Tet. Lett.*,.
[41] R. Badugu, J. R Lakowicz and C. D. Geddes, *Dyes & Pigments*, 64 (2005) 49-55.
[42] R. Badugu, J. R. Lakowicz and C. D. Geddes, *J. Fluorescence*, 13 (2003) 371-374.
[43] M. A. Fox, and M. Chanon, Eds. Photoinduced Electron Transfer, Elseveier, New York, 1998, Part A-D.
[44] G. J. Kavarnos, Fundamentals of Photoinduced Electron Transfer, VCH, New York, 1993.
[45] N. Dicesare and J. R. Lakowicz, *Tetrahedron Lett.*, 43 (2002), 2615-2618.
[46] N. Dicesare and J. R. Lakowicz, *Chem Commun.*, (2001), 2022-2023.
[47] N. Dicesare and J. R. Lakowicz, *Org. Lett.*, 3 (2001)(24), 3891-3893.
[48] Z. F-Kovaceic, M. Miksaj and D. Salamon, *Eur. Food Res. Technol.*, 215 (4) (2002), 347-352.
[49] N. Dicesare and J. R. Lakowicz, *Anal. Biochem.*, 294 (2001), 154-160

That which is claimed is:

1. A method for testing a sample for the presence of a cyanide compound, the method comprising:
    a) reacting at least one boronic acid containing fluorophore with the sample,
    b) illuminating the sample and boronic acid containing fluorophore to generate a fluorescent property; and
    c) observing the sample with means for detecting the fluorescent property, wherein a change in the fluorescent property indicates the presence of cyanide.

2. The method according to claim 1 wherein the presence of the cyanide compound at least partially quenches the fluorescent property of the boronic acid containing fluorophore in a dose dependent manner.

3. The method according to claim 1, wherein the presence of cyanide increases the fluorescent property of the boronic acid containing fluorophore.

4. The method according to claim 1, wherein changes in the fluorescent property is measured by determining the change in intensity or lifetime of fluorescence emission.

5. The method according to claim 4, wherein the degree of change in the fluorescence emission relates to concentration of the cyanide compound and the binding affinity of the cyanide compound to the boronic acid containing fluorophore.

6. The method according to claim 4, wherein the means for observing a fluorescence property response is a camera, a spectofluorometer, a fluorescence microscope, a laser scanner, or a flow cytometer.

7. The method according to claim 6, wherein the cyanide concentration can be sensed at levels less than 20 uM.

8. The method according to claim 1, further comprising the step of determining the concentration of the cyanide compound by comparing the fluorescent property with the fluorescent property obtained with known concentrations of the cyanide compound.

9. The method according to claim 1, wherein the sample comprises living cells or biological fluids.

10. The method according to claim 9, wherein the biological fluid is blood.

11. The method according to claim 1, wherein the sample is a soil or water sample, or is obtained from a soil or water sample.

12. The method according to claim 1, wherein illuminating the sample comprises using an LED light source having an excitation range of about 320 nm to about to 400 nm.

13. The method according to claim 1, wherein the change in fluorescent property is a change in fluorescence emission intensity, fluorescence lifetime, excitation wavelength or emission wavelength.

14. The method according to claim 1, wherein the boronic acid containing fluorophore comprises a heterocyclic quaternary nitrogen (a ring nitrogen) linked through a phenyl ring with a boronic acid moiety.

15. The method according to claim 1, wherein the boronic acid containing fluorophore is

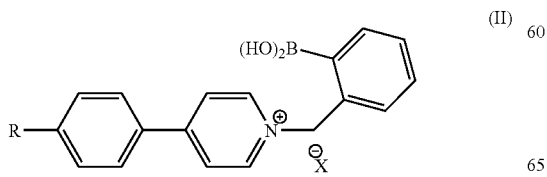

(I)

wherein $R^1$ is H, a straight chain or branched $C_1$-$C_4$ alkyl group, $C_1$-$C_4$ alkoxy group, aryl group, or an amine group $NR^5R^6$, wherein $R^5$ and $R^6$ may be the same as or different from one another and is independently selected from the group consisting of H and $C_1$-$C_4$ alkyl groups, and, $R^2$, $R^3$ and $R^4$ may be the same or different and may be hydrogen or $B(OH)_2$ with the proviso that the compound comprises one $B(OH)_2$ group;

(II)

wherein X is chloride, bromide or iodide, and R is selected from the group consisting of H, straight chain or branched $C_1$-$C_4$ alkyl group, $C_1$-$C_4$ alkoxy group, aryl group, hydroxyl, sulfonyl, and $NR^5R^6$, wherein $R^5$ and $R^6$ may be the same as or different from one another and is independently selected from the group consisting of H and $C_1$-$C_4$ alkyl groups;

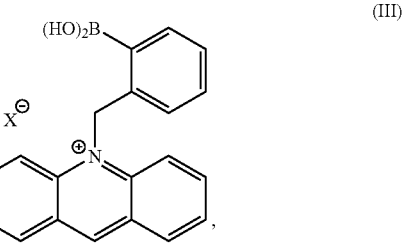

(III)

(IV)

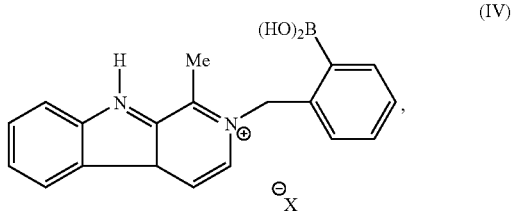

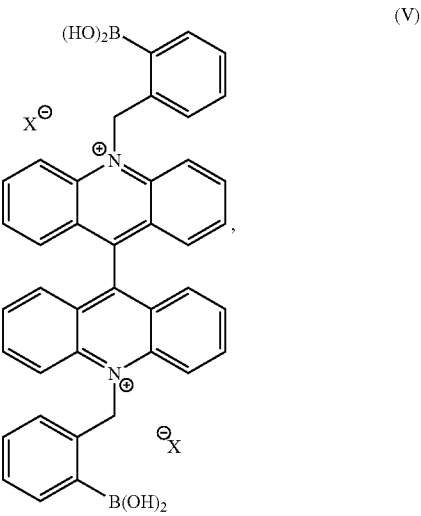

(V)

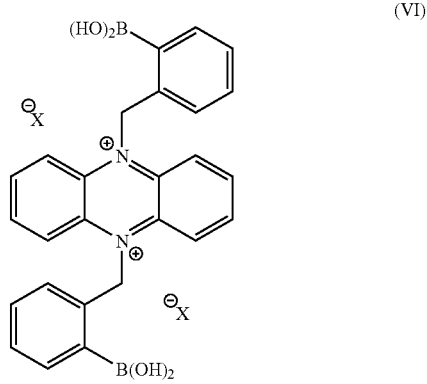

(VI)

wherein X is chloride, bromide or iodide;

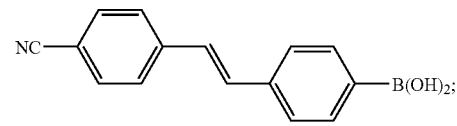

(VII)

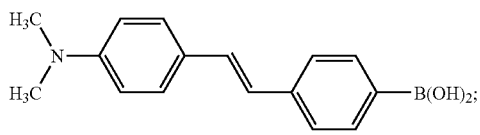

(VIII)

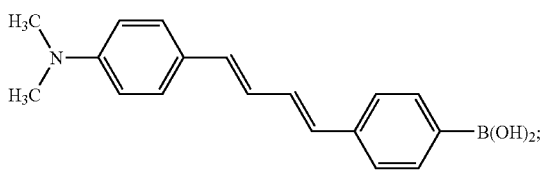

(IX)

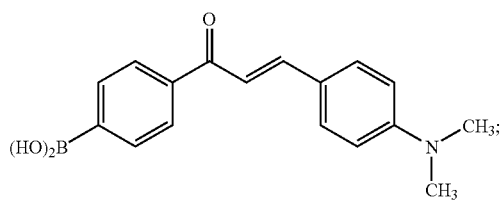

(X)

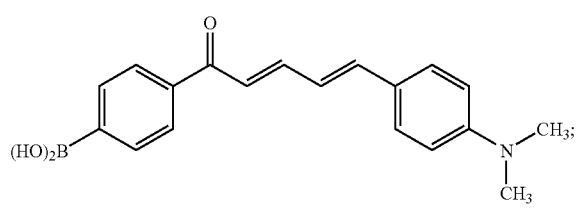

(XI)

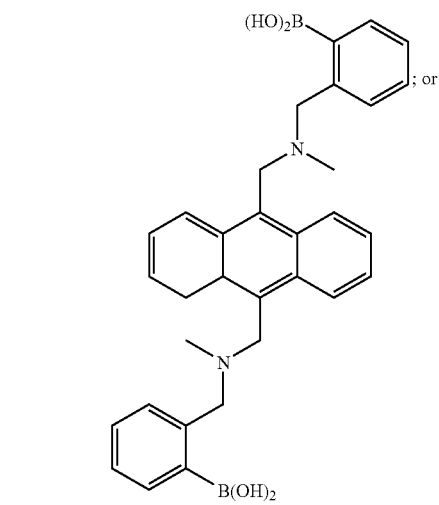

(XII)

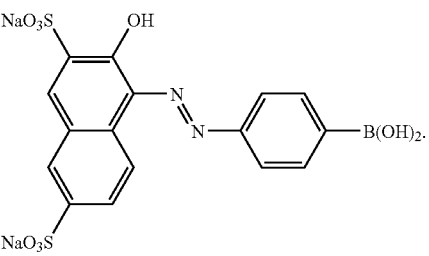

(XIII)

16. The method of claim 1 wherein the change in the fluorescent property is visible in the range of about 5 uM to about 60 uM cyanide concentration.

17. The method according to claim 1, wherein a colorimetric response is visible when cyanide binds to the boronic acid containing fluorophore.

18. The method according to claim 1, wherein the step of observing made remotely by incorporation of the boronic acid containing fluorophore as part of a fiber optic probe, wherein the boronic acid containing fluorophore is attached to a fiber optic probe material.

19. A method for testing a biological or environmental test sample for the presence of a cyanide compound, the method comprising:
   a) reacting a boronic acid containing fluorophore with the sample,
   b) illuminating the sample containing the fluorophore to generate an optical signal; and
   c) observing the sample with means for detecting the optical signal, wherein changes in the optical signal indicates the presence of cyanide, wherein the boronic acid containing is present in a concentration of about 100 nM to about 20 uM; the cyanide is present in a concentration of about 5 uM to about 50 uM; the illuminating step is accomplished using excitation at a range from about 330 to about 370 nm; and the observing step is accomplished using a fluorometer, fluorescence microscope, a laser scanner, or flow cytometer.

20. The method according to claim 19, wherein the optical signal is a wavelength shift that occurs when cyanide binds to the boronic acid containing fluorophore.

21. The method according to claim 19, wherein the illuminating step comprises use of a LED comprising an excitation range from about 320 nm to about 400 nm.

22. The method according to claim 19, wherein the optical signal is a change in color, change in absorbance intensity, change of fluorescence intensity, a spectral shift, or a change in lifetime of fluorescence.

23. A composition solution comprising a test sample suspected of containing a cyanide compound and at least one boronic acid containing fluorophore.

24. The composition according to claim 23, wherein the boronic acid containing fluorophore comprises a heterocyclic quaternary nitrogen linked through a phenyl ring with a boronic acid moiety.

25. The composition according to claim 23, wherein the boronic acid containing fluorophore is

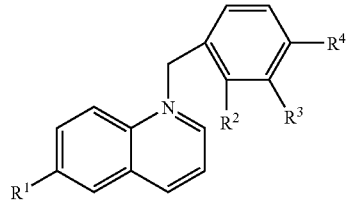
(I)

wherein $R^1$ is H, a straight chain or branched $C_1$-$C_4$ alkyl group, $C_1$-$C_4$ alkoxy group, aryl group, or an amine group $NR^5R^6$, wherein $R^5$ and $R^6$ may be the same as or different from one another and is independently selected from the group consisting of H and $C_1$-$C_4$ alkyl groups, and, $R^2$, $R^3$ and $R^4$ may be the same or different and may be hydrogen or $B(OH)_2$ with the proviso that the compound comprises one $B(OH)_2$ group;

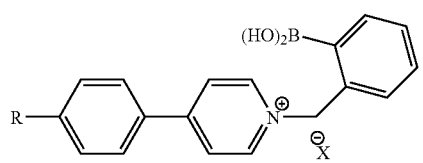
(II)

wherein X is chloride, bromide or iodide, and R is selected from the group consisting of H, straight chain or branched $C_1$-$C_4$ alkyl group, $C_1$-$C_4$ alkoxy group, aryl group, hydroxyl, sulfonyl, and $NR^5R^6$, wherein $R^5$ and $R^6$ may be the same as or different from one another and is independently selected from the group consisting of H and $C_1$-$C_4$ alkyl groups;

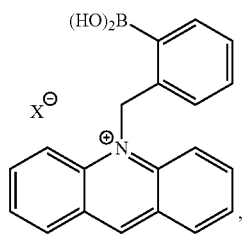
(III)

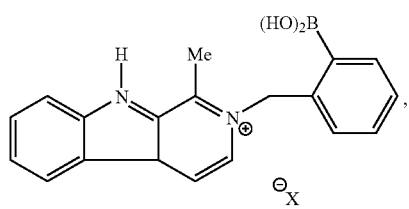
(IV)

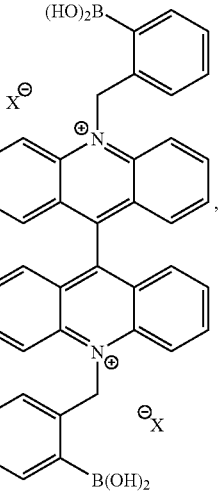
(V)

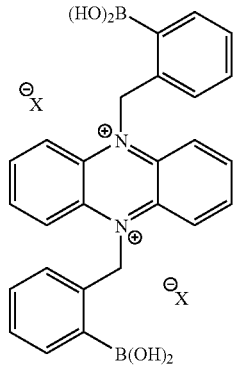
(VI)

wherein X is chloride, bromide or iodide;

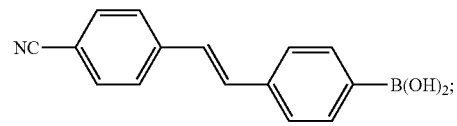
(VII)

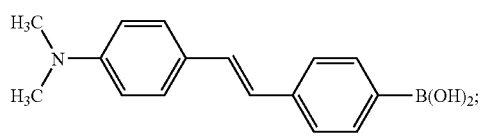
(VIII)

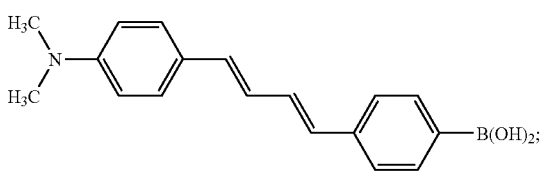
(IX)

-continued

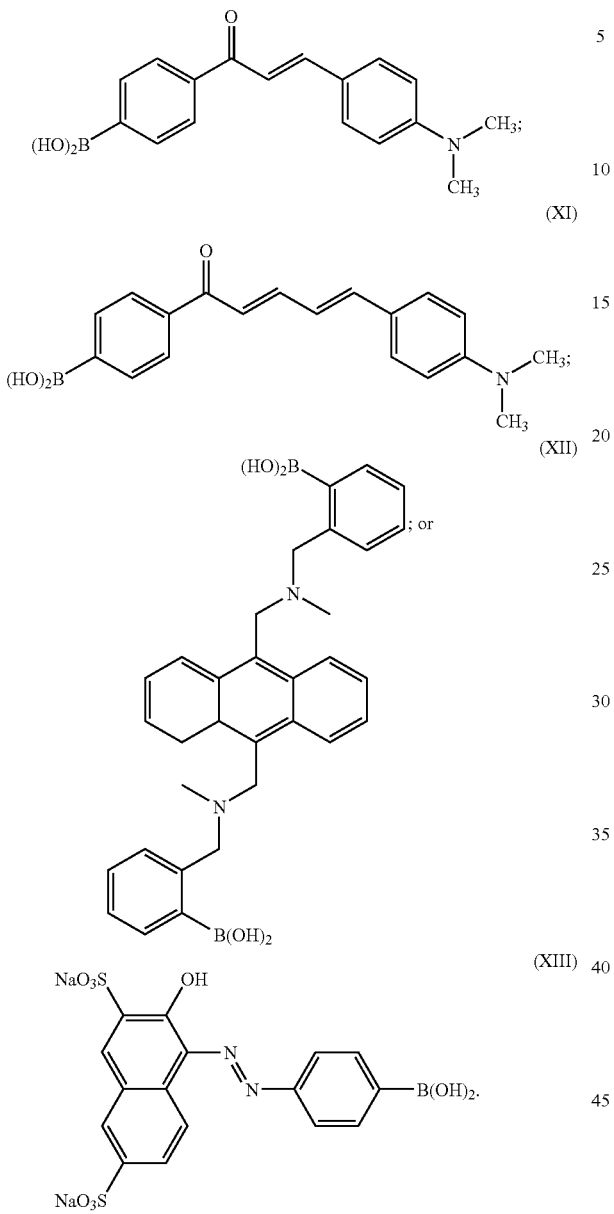

26. A method for testing a sample for the presence of a cyanide compound, the method comprising:

a) reacting at least one boronic acid containing fluorophore with the sample, wherein the boronic acid containing fluorophore is

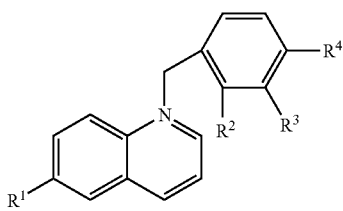

and wherein $R^1$ is a straight chain or branched $C_1$-$C_4$ alkyl group, $C_1$-$C_4$ alkoxy group, aryl group, or an amine group $NR^5R^6$, wherein $R^5$ and $R^6$ may be the same as or different from one another and is independently selected from the group consisting of H and $C_1$-$C_4$ alkyl groups, and, $R^2$, $R^3$ and $R^4$ may be the same or different and may be hydrogen or $B(OH)_2$ with the proviso that the compound comprises one $B(OH)_2$ group;

b) illuminating the sample and boronic acid containing fluorophore to generate a response in a fluorescent property; and c) observing the sample with means for detecting the fluorescent property, wherein a change in the fluorescent property relative to a control value for an unbounded free boronic acid containing fluorophore indicates the presence of cyanide.

27. The method according to claim 26, wherein the boronic acid containing fluorophore is o-BAQBA, -BAQBA, p-BAQBA, o-BMOQBA ,m-BMOQBA, p-BMOQBA, o-BMQBA, m-BMQBA, or p-BMQBA.

28. A kit for detecting and quantifying the amount of cyanide in a test sample, the method comprising:

at least one a boronic acid containing fluorophore in an amount sufficient to react with any cyanide in a test sample, wherein the boronic acid containing fluorophore is adhered to a solid support material, impregnated therein or in solution.

29. The kit according to claim 28, wherein the boronic acid containing fluorophore is attached to a fiber optic probe material or is attached to the fiber optic probe via an intermediate polymer.

30. The kit according to claim 28, wherein the boronic acid containing fluorophore is o-BAQBA, -BAQBA, p-BAQBA, o-BMOQBA ,m-BMOQBA, p-BMOQBA, o-BMQBA, m-BMQBA, or p-BMQBA.

* * * * *

UNITED STATES PATENT AND TRADEMARK OFFICE
CERTIFICATE OF CORRECTION

| | | |
|---|---|---|
| PATENT NO. | : 7,732,215 B2 | Page 1 of 1 |
| APPLICATION NO. | : 10/572344 | |
| DATED | : June 8, 2010 | |
| INVENTOR(S) | : Chris D. Geddes et al. | |

It is certified that error appears in the above-identified patent and that said Letters Patent is hereby corrected as shown below:

Column 1, line 18: "may have" should be -- has --

Signed and Sealed this
Twenty-second Day of February, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,732,215 B2 | |
| APPLICATION NO. | : 10/572344 | |
| DATED | : June 8, 2010 | |
| INVENTOR(S) | : Chris D. Geddes et al. | |

It is certified that error appears in the above-identified patent and that said Letters Patent is hereby corrected as shown below:

On the Title page, item [73]:

Please insert an additional Assignee:

--University of Maryland, Baltimore--

Signed and Sealed this
Twenty-third Day of April, 2013

Teresa Stanek Rea
*Acting Director of the United States Patent and Trademark Office*